(12) United States Patent
Rodriquez

(10) Patent No.: US 11,406,354 B2
(45) Date of Patent: Aug. 9, 2022

(54) STAND-ALONE CONTINUOUS CARDIAC DOPPLER AND ACOUSTIC PULSE MONITORING PATCH WITH INTEGRAL VISUAL AND AUDITORY ALERTS, AND PATCH-DISPLAY SYSTEM AND METHOD

(71) Applicant: Gerardo Rodriquez, Apo, AE (US)

(72) Inventor: Gerardo Rodriquez, Apo, AE (US)

( * ) Notice: Subject to any disclaimer, the term of this patent is extended or adjusted under 35 U.S.C. 154(b) by 344 days.

(21) Appl. No.: 16/508,885

(22) Filed: Jul. 11, 2019

(65) Prior Publication Data
US 2019/0388056 A1 Dec. 26, 2019

Related U.S. Application Data

(63) Continuation-in-part of application No. 15/834,044, filed on Dec. 6, 2017, now Pat. No. 10,835,205.
(Continued)

(51) Int. Cl.
*A61B 8/00* (2006.01)
*A61B 5/00* (2006.01)
(Continued)

(52) U.S. Cl.
CPC ............ *A61B 8/4236* (2013.01); *A61B 5/742* (2013.01); *A61B 8/02* (2013.01); *A61B 8/065* (2013.01);
(Continued)

(58) Field of Classification Search
CPC ......... A61B 8/00; A61B 8/4281; A61B 8/488; A61B 8/02; A61B 8/56; A61B 5/02;
(Continued)

(56) References Cited

U.S. PATENT DOCUMENTS 3,547,107 A * 12/1970 Gofman ................. A61B 5/332
600/518
4,666,441 A * 5/1987 Andriola .............. A61K 9/7084
424/448
(Continued)

*Primary Examiner* — Oommen Jacob
(74) *Attorney, Agent, or Firm* — Duncan Palmatier

(57) ABSTRACT

A stand-alone continuous cardiac Doppler or acoustic pulse monitoring patch provides visual and auditory signals that a pulse or heartbeat is detected or not detected in a human subject. The invention is a small patch with a peel-away adhesive surface that is applied to the skin of the subject, preferably near a large artery. For the Doppler monitor, the patch includes a pad formed of a conductive medium to enhance transmission and reception of ultrasonic waves. For the acoustic monitor, the pad has a sound focusing portion that permits entry of sounds and focuses the sounds toward a microphone, and the pad also has a sound insulating portion surround the sound focusing portion. The patch includes an integral power source. The Doppler patch has transmitters and receivers to send and detect reflected ultrasonic waves and a transducer to convert the reflected waves into an electrical signal. The acoustic patch has a microphone to detect the sound of a heartbeat and a transducer to convert the sound energy into an electrical signal. A processor analyzes the Doppler wave signals or the acoustic signals. A light indicates the presence and strength of a pulse detected from the Doppler wave signals or a heartbeat detected by the microphone. A speaker and a vibrator may also to indicate the presence and strength of a pulse or a heartbeat. The Doppler effect of waves reflecting from blood pumped from a heart is used to detect a pulse in the subject. The presence of a pulse or heartbeat is analyzed by the processor to determine the frequency and strength of blood flow or beating of the heart. The processor causes the light, speaker or vibrator to blink, beep or vibrate at a rate to indicate the frequency of rhythmic blood flow or heartbeat.

12 Claims, 12 Drawing Sheets

Related U.S. Application Data

(60) Provisional application No. 62/523,765, filed on Jun. 22, 2017, provisional application No. 62/430,822, filed on Dec. 6, 2016.

(51) Int. Cl.
*A61B 8/02* (2006.01)
*A61B 8/06* (2006.01)
*A61B 8/08* (2006.01)

(52) U.S. Cl.
CPC ............ *A61B 8/488* (2013.01); *A61B 5/6833* (2013.01); *A61B 8/0866* (2013.01); *A61B 8/4281* (2013.01); *A61B 8/56* (2013.01)

(58) Field of Classification Search
CPC ..... A61B 5/683; A61B 5/6833; A61B 8/0866; A61B 5/026; A61B 8/4236; A61H 31/004; A61H 31/00; A61H 2230/30; A61H 2230/25; A61H 2201/5058; A61H 2201/0188; A61H 2201/1207; A61H 2201/1609; A61H 2201/1619; A61H 2201/50; A61H 2201/5025; A61H 2201/5048
See application file for complete search history.

(56) References Cited

U.S. PATENT DOCUMENTS

| Patent/Pub. No. | | Date | Inventor | Class |
|---|---|---|---|---|
| 6,341,229 | B1* | 1/2002 | Akiva | A61B 5/282 600/388 |
| 2002/0058721 | A1* | 5/2002 | Pachl | C08J 9/0061 521/135 |
| 2006/0030781 | A1* | 2/2006 | Shennib | A61B 5/318 600/509 |
| 2006/0047215 | A1* | 3/2006 | Newman | A61N 1/0492 600/513 |
| 2006/0129067 | A1* | 6/2006 | Grajales | A61B 7/04 600/586 |
| 2009/0316925 | A1* | 12/2009 | Eisenfeld | A61B 7/008 381/67 |
| 2011/0137209 | A1* | 6/2011 | Lahiji | A61B 7/026 600/586 |
| 2012/0209131 | A1* | 8/2012 | Jones | A61B 7/04 600/528 |
| 2013/0030259 | A1* | 1/2013 | Thomsen | A61B 5/02028 600/301 |
| 2016/0015359 | A1* | 1/2016 | Emmanouilidou | A61B 7/04 600/529 |
| 2016/0120433 | A1* | 5/2016 | Hughes | A61B 5/335 600/483 |
| 2019/0388056 | A1* | 12/2019 | Rodriquez | A61B 8/488 |

* cited by examiner

STAND-ALONE CONTINUOUS CARDIAC DOPPLER AND ACOUSTIC PULSE MONITORING PATCH WITH INTEGRAL VISUAL AND AUDITORY ALERTS, AND PATCH-DISPLAY SYSTEM AND METHOD

CLAIM OF PRIORITY TO NON-PROVISIONAL AND PROVISIONAL APPLICATIONS (35 U.S.C. §§ 120 AND 119(E))

Pursuant to 35 U.S.C. § 120 and 37 CFR 1.78(d)(2), this application is a continuation-in-part of prior non-provisional patent application Ser. No. 15/834,044 filed on Dec. 6, 2017 ("the '044 Non-Provisional application"). The '044 Non-Provisional application claimed priority, under 35 U.S.C. § 119(e), from provisional patent Application No. 62/430,872 filed on Dec. 6, 2016, and from provisional application No. 62/523,765 filed on Jun. 22, 2017. Accordingly, this continuation-in-part application is entitled to the benefit of these provisional applications. The Ser. No. 15/834,044 non-provisional application and the 62/430,872 and 62/523,765 provisional applications are incorporated herein by reference.

FIELD OF THE INVENTION

The present invention relates to a stand-alone continuous cardiac Doppler and acoustic pulse monitoring patch that provides visual and auditory signals that blood flow is detected in a subject. More specifically, the Doppler pulse monitoring patch of the present invention is a small patch that is applied to the skin of a subject, preferably near a large artery, and thereafter generates visual and audible signals indicating the presence or absence of blood flow and, if blood flow is detected, the frequency and strength of the flow. Similarly, the Acoustic pulse monitoring patch of the present invention is a small patch that is applied to the skin of a subject, preferably over the heart, and thereafter generates visual and audible signals indicating the presence or absence of blood flow and, if blood flow is detected, the frequency and strength of the flow. The invention is intended for use by emergency medical technicians, nurses, and doctors as a fast and reliable means to detect a pulse and, if called for, initiate appropriate medical procedures, such as cardiopulmonary resuscitation (CPR).

BACKGROUND OF THE INVENTION

According to the American Heart Association (http://cpr.heart.org/AHAECC/CPRAndECC/General/UCM_477263_Cardiac-Arrest-Statistics.jsp), in the United States, since 2012, over half a million people have experienced cardiac arrest each year. Of those, about sixty percent occurred outside a hospital and almost half of these involved the application of CPR by a lay person. The survival rate for those out-of-hospital cardiac arrests was about ten percent. The survival rate for cardiac arrests in a hospital was also low at under thirty percent. A critical component of surviving cardiac arrest is quick treatment, such as the application of CPR. The decision to initiate CPR or other procedures to treat cardiac arrest is highly time sensitive. The likelihood of survival decreases by ten percent for every minute from the absence of a pulse to the return of spontaneous circulation (ROSC).

But, the physical palpitation of a pulse, usually by placing one or more fingers over a subject's artery, is difficult and subject to substantial error. In one study, forty-five percent (66 out of 147) of medically trained first responders were unable to identify a pulse despite a carotid pulse and a blood pressure (BP) above or equal to 80 mmHg Only fifteen percent (31 out of 206) of participants produced a correct diagnosis of the absence of a pulse within ten seconds, which is the recommendation of the American Heart Association.

The use of an electrocardiograph (ECG) to detect a pulse is common, but problematic, because the widely-recognized graphical pattern measures electrical emissions from the heart muscle. But, these electrical signals detected by the ECG do not measure the flow of blood in the subject and it is not uncommon for telemetry to detect favorable electrical emissions from the heart, even after the flow of blood has ceased and, in some instances, the subject has perished.

As noted above, physical palpitation for a pulse is widely used, but is also substantially unreliable. Other means to detect blood flow include Doppler pulse monitors, which have become more common in recent years, especially with the popularity and availability of fetal heart monitors sold at low prices to the general public. These monitors are designed for intermittent checks. A typical Doppler monitor has an ultrasound wand connected to a hand-held box by a cord. A conductive gel, to enhance transmission and reception of the ultrasonic waves, is squirted onto the head of the wand which is placed against the subject. The box amplifies the rhythmic sound of pulsing blood. But, such a device must be held by a technician and cannot be secured in place to provide constant, real-time information. This continuing real-time information is helpful for monitoring dynamic changes in an unstable or potentially unstable patient. For example, when CPR is administered, a hand-held Doppler monitor cannot be held in place without another technician and, even if another technician is available to hold the monitor in place, the movement of the patient undergoing CPR makes holding the wand in place and receiving useful return signals is extremely difficult. Yet, having real-time blood flow information is very helpful to a person performing CPR, because it can inform the technician that CPR has succeeded in achieving ROSC or that the patient is relapsing.

Similarly, recent developments in electronic stethoscopes have made available stethoscopes with electronic acoustic sensors to detect the sound of a beating heart and analyze the sound with a processor which in turn displays the heartbeat waveform on a screen. As with the Doppler monitors, these acoustic stethoscopes must be held in place and a separate display must be observed to see the heartbeat waveform, making it awkward to administer CPR while continuing to monitor real-time information. These electronic stethoscopes can also monitor a subject's breathing, which can identify shallow breathing, seen in overdose states such as alcohol poisoning or opiate overdose, and apnea, the absence of breathing. With the rapid increase in opiate-related overdoses and deaths, there is a need for a monitor that is easily and quickly applied to provide constant, real-time detection of a subject's breathing without reliance on external devices.

Even in the hospital setting existing devices pose problems. For example, when a subject requires an X-ray or other scan, existing ECG, Doppler, and acoustic monitors must usually be removed, leaving medical personnel without direct information about the subject's blood flow. As noted above, since the passage of even very short periods of time can drastically reduce the chance of survival from cessation of blood flow, the lack of direct information can be a significant contributor to mortality.

Identifying and tracking the mechanical blood flow of the heart and large arterial vessels in real time is underutilized and important. The current system of isolated finger pulse or Doppler pulse checks is challenging, even for medical professionals.

Needed is a pulse monitor that is easily and quickly applied to provide constant, real-time detection of a subject's blood flow without reliance on external devices.

SUMMARY OF THE INVENTION

The present invention discloses a stand-alone continuous cardiac Doppler and acoustic pulse monitoring patch that provides visual and auditory signals that a pulse is detected or not detected in a subject. The invention is a small patch with a peel-away adhesive surface that is applied to the skin of a subject. The Doppler monitor should be applied near a large artery and the acoustic monitor should be applied over the heart. The adhesive surface of the patch secures the monitor to the skin of the patient and also includes a layer of material, such as gel, to provide a conductive medium for the Doppler monitor, to enhance transmission and reception of ultrasonic waves, or sound isolation for the acoustic monitor, to enhance reception of heartbeats and insulate against or absorb unwanted sounds. The patch includes a power source, electronics associated with the Doppler or acoustic signals, a processor to control and analyze the signals, a memory, and one or more of a light, speaker, or vibration generator to indicate the presence and strength of a pulse.

The electronics of the Doppler patch include transmitters and receivers to send and detect reflected ultrasonic waves, a transducer to convert an electrical signal into ultrasonic waves and convert the reflected waves into an electrical signal, a processor to control and analyze the signals, and a memory to store a subject's pulse signals as well as models of signal patterns to which the subject's measured signals may be compared. The Doppler effect of waves reflecting from moving blood or a pulsing artery is used to detect a pulse in the subject. The presence of a pulse is analyzed by the processor to determine the frequency and strength of blood flow. The processor causes a light to blink at a rate to indicate the frequency of rhythmic blood flow. In a further embodiment, the processor analyzes the strength of the blood flow and causes the light to increase or decrease in intensity to reflect the strength or weakness of the mechanical function of the heart. The processor may also drive a speaker to emit sounds, such as beeps, that indicate the frequency and strength of blood flow. In addition, a vibrator can be added to indicate the frequency and strength of blood flow by touching to patch. The absence of blood flow may be indicated by the absence of light or sound or vibration, or by separate or different light or auditory or vibratory signals intended to convey the absence of blood flow and potential emergency.

In an alternative embodiment, the continuous cardiac Doppler pulse monitoring patch can be in the form of a "butterfly" patch designed to straddle a subject's throat to monitor both left and right carotid arteries. In this butterfly patch embodiment, Doppler ultrasonic signals are transmitted and received from each side of the butterfly patch, one over the left carotid artery and the other over the right carotid artery. The Doppler signals detect the presence or absence of blood flow and pulse from each carotid artery and the information is processed, as described above. The processed flow and pulse information can be displayed visually with a light mounted in the middle of the butterfly patch, over the subject's throat, as well as audibly with a speaker, as described above. This butterfly patch arrangement can be useful if a cervical collar has been placed around the patient's neck, because the visual and audible signals of the patch can be seen through the front opening provided in most cervical collars.

The electronics of the acoustic patch include a microphone to detect sound waves, a transducer to convert the received sound waves to electrical signals, a processor to analyze the signals, and a memory to store a subject's heartbeat signals as well as models of signal patterns to which the subject's measured signals may be compared. The presence of a heartbeat is analyzed by the processor to determine its frequency and strength. The processor causes a light to blink at a rate to indicate the frequency of the heartbeat. In a further embodiment, the processor analyzes the strength of the blood flow and causes the light to increase or decrease in intensity to reflect the strength or weakness of the heartbeat. The processor may also drive a speaker to emit sounds, such as beeps, that indicate the frequency and strength of the heartbeat. In addition, a vibrator can be added to indicate the frequency and strength of the heartbeat by touching to patch. A weak or failing heartbeat, or the absence of a heartbeat, may be indicated by the absence of light or sound or vibration, or by separate or different light or auditory or vibratory signals intended to convey the absence of a heartbeat and potential emergency. In a further embodiment, the acoustic monitor also listens for a subject's breathing and the processor analyzes detected sounds to identify known breathing patterns associated with symptoms of distress, such as shallow breathing, which is an indicator of an overdose state from opiates or alcohol poisoning, or apnea. As with recognized indicators of cardiac distress, the processor can drive the light, speaker or vibrator to indicate the frequency and strength of the subject's breathing.

In an alternative embodiment, an integrated continuous cardiac Doppler or acoustic pulse monitoring patch includes a port to connect the patch by conductive wires to a separate display unit that can receive the blood flow and pulse data from the patch and display the data visually on a screen as well as provide auditory or vibratory signals. The display unit can further process the data and display heart pulse (bpm) and blood flow (cm/s) rates in numerical and graphic forms. In a further embodiment, the patch and display unit can each include wireless transceivers to connect them and communicate the data wirelessly. In yet a further embodiment, the display unit can provide processing and power for the patch, which is consequently simplified and less expensive. In another embodiment, a simplified patch will have transducers to transmit and receive ultrasound waves and its own integrated power and wireless communication capability, thereby allowing the simplified patch to provide Doppler or acoustic signal data wirelessly to the display unit, which will process and display the data.

The invention is intended for use by emergency medical technicians, nurses, and doctors as a fast and reliable means to detect a pulse and, if called for, initiate appropriate medical procedures, such as cardiopulmonary resuscitation (CPR).

DETAILED DESCRIPTION

Figure 1:
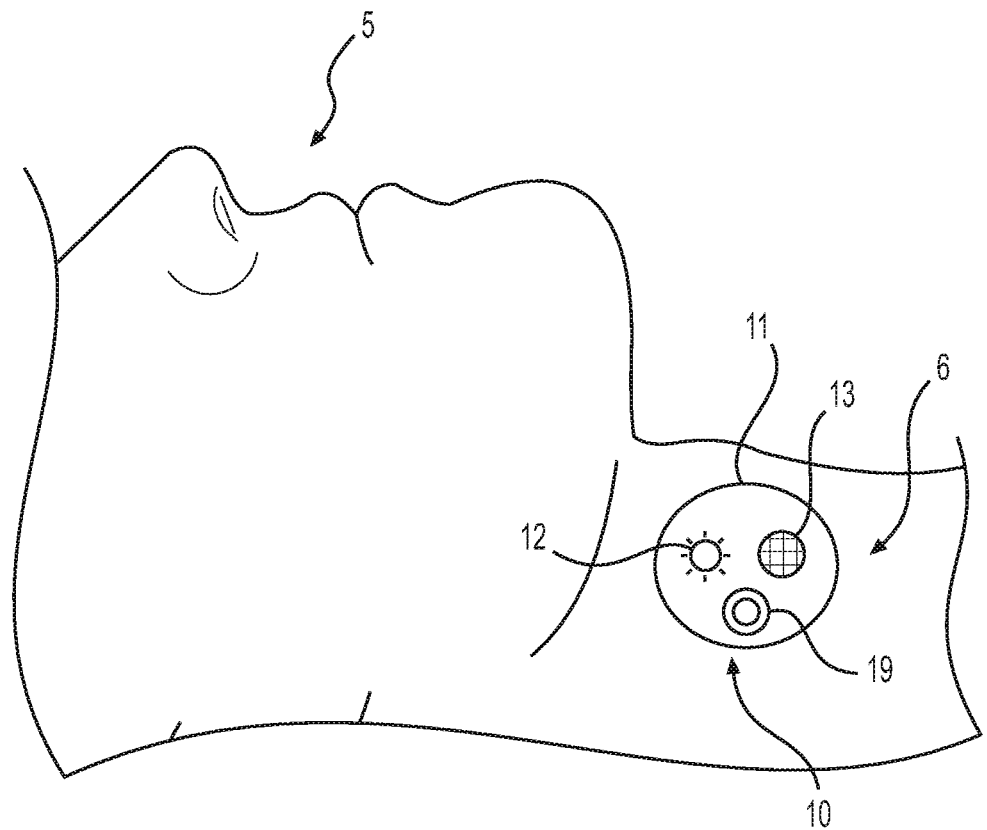
FIG. 1 shows a stand-alone continuous cardiac Doppler pulse-monitoring patch with visual and auditory alerts of the present invention applied to the neck of a patient.
Figure 5:
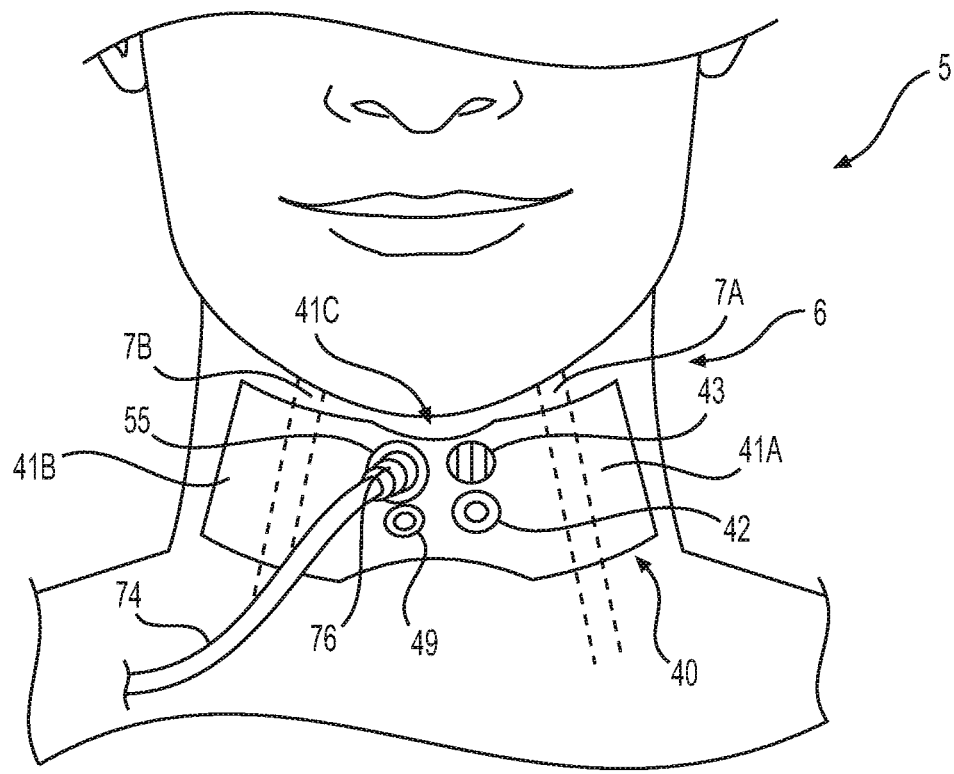
FIG. 5 shows a butterfly patch embodiment of the stand-alone pulse-monitoring patch invention applied to the neck of a patient.
Figure 6:
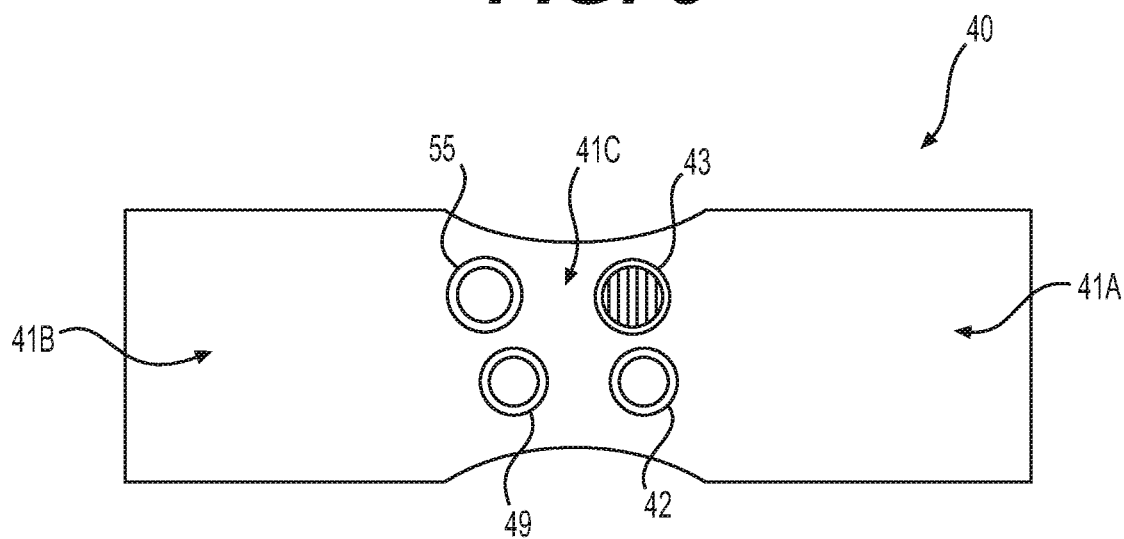
FIG. 6 is a top view of the stand-alone pulse-monitoring butterfly patch invention.
Figure 7:
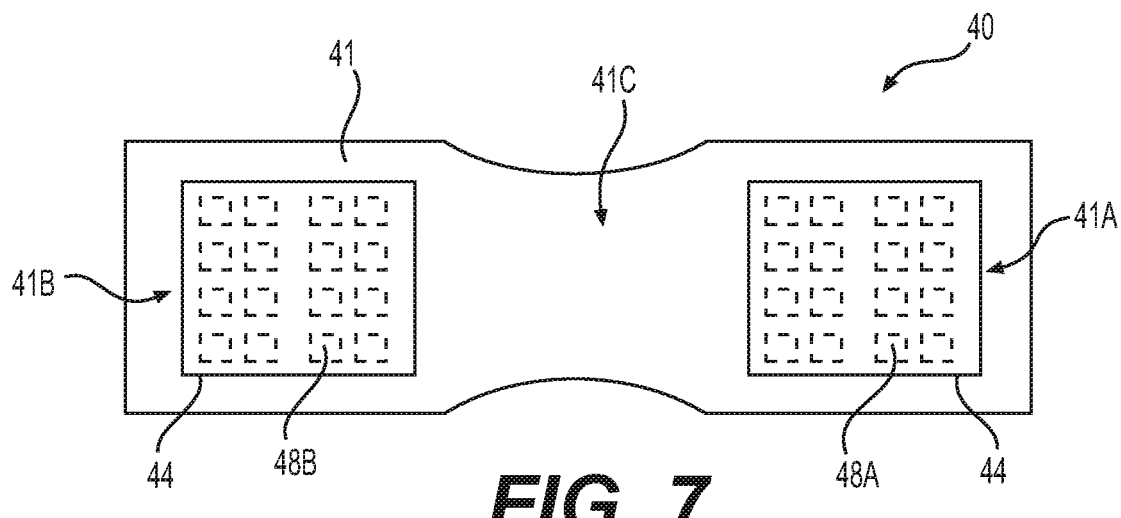
FIG. 7 is a bottom view of the stand-alone pulse-monitoring butterfly patch invention.

FIG. 1 shows the stand-alone continuous Doppler heart monitor patch 10 applied to the side of the neck of a patient 5. In this position, the monitor 10 will be close to the subject's neck artery 6, the right common carotid artery 7B shown in FIG. 5, which is one of the better arteries for detecting a pulse. The carotid artery is a useful position to detect pulse, since it leaves the subject's chest free for CPR or other procedures to address cardiac arrest. The monitor 10 may be placed over other arteries, such as the femoral or radial arteries. When the on/off switch 19 is turned to the on position, the monitor 10 is placed over the subject's neck artery 6 and will begin transmitting ultrasonic signals and detecting their reflections. When blood is flowing, the Doppler effect on the reflected signals will be identified by the monitor's 10 circuitry (16 in FIGS. 2 and 3), described below, as indicative of the blood's flow velocity, as well as of the frequency of pulses as pulsations of the blood from the heart's pumps is recognized. This rhythmic pulse will be indicated by a blinking light 12 and may further be indicated by an audible sound, such as a beep, from a speaker 13.

Figure 2:
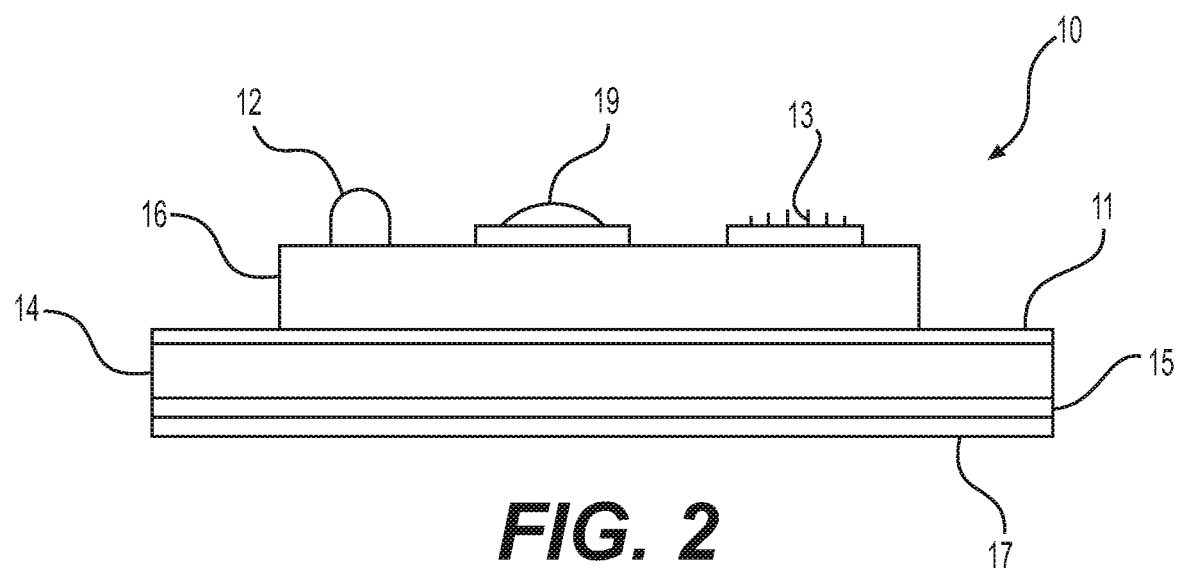
FIG. 2 is a side view showing the layers the stand-alone pulse-monitoring patch.

FIG. 2 illustrates the parts of the monitor patch 10. The bottom of the monitor patch 10 is formed by a base 11, which supports the circuitry 16. Under the base 11 is a conductive pad 14 to enhance transmission and reception of the ultrasonic waves from the circuitry 16 to the patient 5. The conductive pad 14 may be a thermoplastic gel or a hydrogel. Hydrogels are hydrophilic networks of polymer chains and may be free-standing or contained within a thin membrane. Beneath the conductive pad 14 is a thin adhesive layer 15 to fix the monitor patch 10 to the subject's skin. A peel-off layer 17 is disposed over the adhesive layer 15 to cover and preserve the adhesive until used. Mounted on the base 11 is the circuitry 16, described below. The circuitry 16 may be mounted on a printed circuit board (PCB), which may be rigid, but, in a preferred embodiment, has some flexibility to conform to the subject's body contours. Over the circuitry 16 are a light 12 and a speaker 13 and, in some embodiments, a manual on/off switch 19. A conductor 29 from the circuitry 16 to the light 12 allows electricity to flow to the light 12. Similarly, a conductor 30 controls electrical flow to the speaker 13, and conductors 31 provide connectivity between the on/off switch 19 on the circuitry 16.

Figure 3:
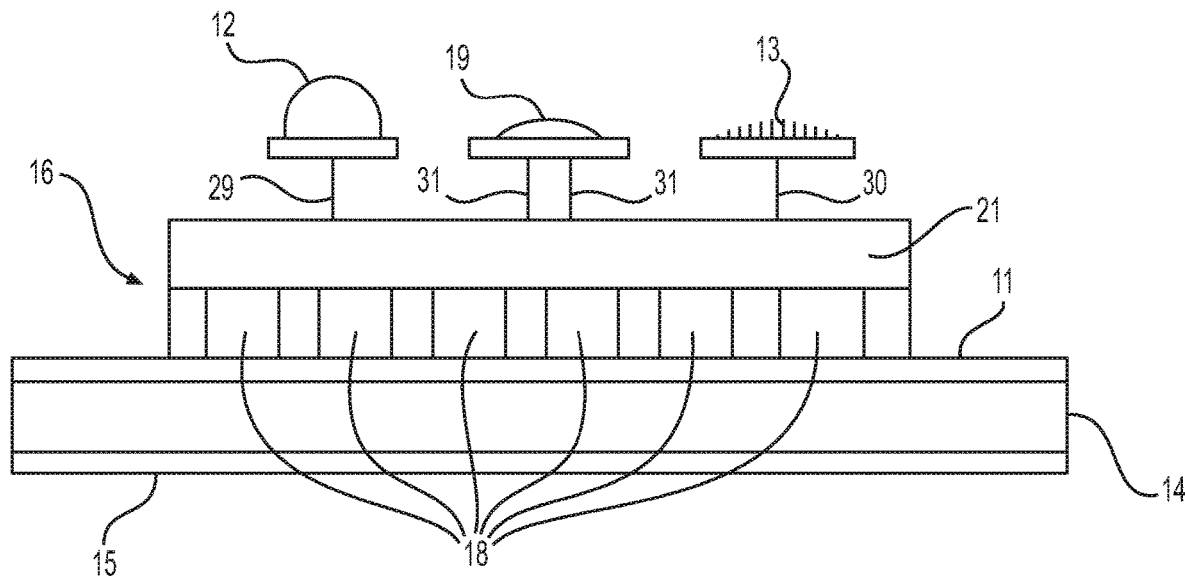
FIG. 3 is a side, cut-away view showing the arrangement of components of the stand-alone pulse-monitoring patch invention.
Figure 4:
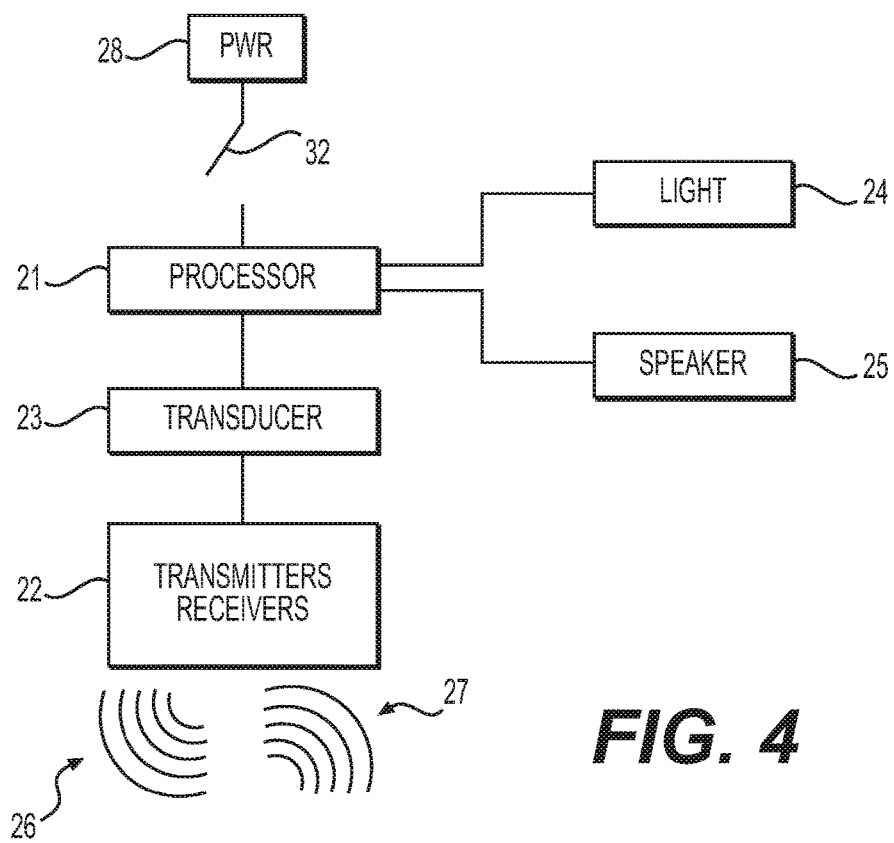
FIG. 4 is a block diagram of the electronic circuitry of the stand-alone pulse-monitoring patch invention.

FIGS. 3 and 4 show more detail of the circuitry 16. A power source 28, such as a small battery, provides integrated power to the electronic components of the stand-alone monitor patch 10. A switch 32 controls power or can activate the circuitry 16 from a low-power consumption rest state. A transducer 23 includes transmitters/receivers 18 arrayed in or over the base 11. The transmitters emit ultrasonic waves 26 and the receivers detect reflected waves 27. The reflected wave signals 27 are demodulated and analyzed by a processor 21 to determine whether the reflected wave pattern corresponds with Doppler shift signals indicative of flowing blood. Since blood from a heart is pumped in rhythmic pulses, the received Doppler shift signals will indicate that pattern. The processor 21 incorporates memory that can include data of Doppler shift signals indicative of flowing or pulsing blood. By comparing the Doppler shift signals 27 from the transducer 23 with data stored in the memory associated with the processor 21, the processor determines whether blood flow has been detected. Once a blood flow is detected, the processor 21 causes a light 12 (24 in FIG. 4) to blink in synchronization with the rhythm of the heart's pulses. Similarly, the processor 21 will cause a speaker 13 (25 in FIG. 4) to emit a sound, such as a beep, in synchronization with the rhythm of the heart's pulses. The processor 21 will also analyze the reflected wave signals 27 for their strength by comparing them to known values stored in the processor's 21 memory. Using the stored values, the processor 21 will cause the light 12 to blink with an intensity corresponding to the strength or weakness of the detected pulse. Similarly, based on the stored values, the processor 21 will cause the speaker 13 to beep with a volume corresponding to the strength or weakness of the detected pulse.

The light 12 may be an LED. In a preferred embodiment, the LED light 12 is capable of emitting different colors of light, such as red and green. For example, if a healthy pulse is detected by the monitor patch 10, the processor 21 will cause the light 12 to blink with a green color indicating a healthy pulse, but if a weak pulse is detected, the processor 21 will cause the light 12 to emit a yellow or red color. Alternatively, two or more lights 12 may be employed, each chosen to emit a different color. As described above, the processor 21, relying on values stored in the processor's memory, will cause the intensity of the light to increase or decrease, or the color of the light to change, in relation to the strength or weakness of the detected pulse. Similarly, the processor 21 will cause the speaker 13 to increase or decrease the volume, or change another characteristic of the emitted sound in relation to the strength or weakness of the detected pulse. If the processor 21 detects a weak or declining pulse, the processor 21 will cause a color-changing LED light 12 to change in color, for example from green to red, or will shift the visual indicator from one color (e.g., green) light to a different color (e.g., yellow or red) light. Similarly, the processor 21 may cause the speaker 13 to emit a different sound as a weak or declining pulse is detected. If a pulse is lost, the processor 21 can cause a color-changing LED light 12, or a separate light, to emit a continuous bright, emergency red light. Similarly, if no pulse is detected or if a pulse signal fades completely, the processor 21 may cause the speaker 13 to emit a shrill continuous emergency sound.

In operation, the continuous cardiac Doppler monitor patch 10 will be applied to a patient 5 when a continuous pulse needs to be identified. The monitor patch 10 is activated or turned on by a switch 19, the peel-off layer 17 is removed, exposing the adhesive 15, and the monitor patch 10 is placed over a subject's 5 artery 6. It will be appreciated that the sequence of activating the switch 19 and removing the peel-off layer 17 may be reversed. In an alternative embodiment, the removal of the peel-off layer 17 will turn on or activate the circuitry 16 of the monitor patch 10, either by turning a switch 19 to the active "on" position or by closing the on/off circuit 32 to the power source 28. By deactivating the circuitry 16 of the monitor patch 10, or cutting off power from the power source 28, the switch 19 allows the monitor patch 10 to be inactive for long periods of time, such as during storage, yet be available in an instant when needed. When the monitor patch 10 is turned on, the processor 21 will direct the transducer 23 to send and receive ultrasonic signals, 26 and 27, from the transmitters/receivers 18. The transmitted and received signals, 26 and 27, may be combined, or the reflected signals 27 alone may be analyzed by the processor 21 and compared to values stored in the processor's 21 memory. If the combined, 16 and 27, or reflected signals 27 correspond to a stored value for blood pumped by a heart, the processor 21 will cause the light 12 to blink in synchronization with the pulse and with an intensity corresponding to the strength or weakness of the pulse. Similarly, the processor 21 will cause the speaker 13 to beep in synchronization with the pulse and with a volume corresponding to the strength or weakness of the pulse.

The monitor patch 10 may be used on unstable patients or patients with the potential of instability. Identifying the absence of a pulse is paramount to initiating CPR. The monitor patch 10 can also be applied while patients 5 are in motion. For example, moving patients 5 down stairs or transporting patients 5 in a helicopter. Moving patients 5 downstairs requires that the transporting personnel be at the head and foot of the stretcher, where they are unable to verify a continuous pulse. Similarly, air medical evacuations, and even automotive transportation, are loud and vibrations distracting, interfering with the detection of a pulse. For example, it is difficult to feel a pulse or auscultate a heart beat in a helicopter. The monitor patch 10 uses a light 12 as proof of a heart beat and pulse. Moreover, in low visibility environments, the monitor patch 10 uses a speaker 13 as proof of a heart beat and pulse.

The monitor patch 10 will, preferably, be placed on a large artery 6, such as the carotid, radial, or femoral arteries. The monitor patch 10 can be also located on the chest wall, since the ejection of blood from the aortic valve can be captured by the reflected Doppler signal 27. Ideally, the monitor patch 10 will be placed on the patient's 5 left carotid artery 6 (7A in FIG. 4). The left carotid will be the most common site of placement because of infrequent procedural use, a large pulse wave, and its location away from the patient's 5 chest. The chest is needed for ECGs, defibrillator pads, and chest compressions. The monitor patch 10 of the present invention is designed as a stand-alone that integrates the switch 19, light 12, speaker 13, circuitry 16, base 11, conductive pad 14, and adhesive layer 15 into a unitary and compact device configured to conform and adhere to the contours of a subject's 5 skin above an artery 6. Ideally, a small patch of about 2½ inches in diameter, or about 5 square inches, will conform easily to the contours of the patient's skin and reside over an area where arterial blood may be detected. Stand-alone monitor patches of the invention may be larger to provide more space for circuitry and cover greater area over an artery, such stand-alone monitor patches are not limited in size, but a larger patch will be cumbersome and difficult to apply. It is preferred, but not required that stand-alone monitor patches cover areas of less than about twenty square inches.

The monitor patch 10 will be able to generate visual 12 and auditory 13 signals. The signal will increase and decrease in intensity based on the pulse wave generated by the heart. This enables the medical provider to determine if the patient's 5 pulse is strong, weak, or absent. The signals (light & sound) also vary in intensity with a diminishing or increased pulse wave. This enables the medical provider to determine if a pulse is weakening or stopping and the provider will be able to take appropriate actions and determine if a treatment is working by an increased pulse signal.

The monitor patch 10 of the present invention can monitor dynamic changes in unstable or potentially unstable patients. With this information the medical provider can use the intensity of the light/sound signal to closely follow the pulse wave and mange therapy in real time. This feature is especially helpful in evaluating the effectiveness of CPR. A strong signal will signify adequate CPR, improving success to Return of Spontaneous Circulation (ROSC).

The monitor patch 10 can also detect blood flow to an extremity, thereby providing information about the exact time of ischemia (inadequate blood flow) or changes in blood flow. This can be used to monitor for compartment syndrome, violation of the neurovascular bundle, or an embolic event to a large extremity.

The invention also provides a simple continuous cardiac Doppler monitor patch 10 for checking fetal distress in pregnancy.

FIGS. 5 through 9 show an alternative embodiment of the stand-alone continuous cardiac Doppler pulse monitoring patch that provides visual and auditory signals that a pulse is detected or not detected in a subject. In this embodiment, the patch 40 is shaped in a "butterfly" configuration to straddle a subject's throat so that each wing, 41A and 41B, covers that part of the throat over the left 7A and right 7B carotid arteries. In this position, the monitor 40 detects a pulse from either the left 7A or right 7B carotid arteries or both. As noted previously, the carotid artery is a useful position to detect pulse, since it leaves the subject's chest free for CPR or other procedures to address cardiac arrest.

The butterfly monitor patch 40 may be placed over other arteries, such as the femoral or radial arteries. Each wing, 41A at the left and 41B at the right, of the butterfly patch 40 includes an array of transmitters/receivers, 48A and 48B, respectively. As described above, the transmitters of each array, 48A and 48B, emit ultrasonic waves, 66A at the left and 66B at the right, and the receivers, 67A at the left and 67B at the right, detect reflected waves. The reflected wave signals, 67A and 67B, are demodulated and analyzed by a processor 61 to determine whether the reflected wave pattern corresponds with Doppler shift signals indicative of flowing blood, as described above. Since blood from a heart is pumped in rhythmic pulses, the received Doppler shift signals will indicate that pattern and the memory in association with the processor 61 will provide data of models indicative of heart pulse patterns. Once a blood flow is detected, the processor 61 may cause a light 42 to emit light or blink in synchronization with the rhythm of the heart's pulses. Similarly, the processor 61 may cause a speaker 43 to emit a sound, such as a beep, in synchronization with the rhythm of the heart's pulses. As noted above, the processor 61 will also analyze the reflected wave signals, 67A and 67B, for their strength by comparing them to known values stored in the processor's 61 memory. Using the stored values, the processor 61 will cause the light 42 to blink with an intensity corresponding to the strength or weakness of the detected pulse. Similarly, based on the stored values, the processor 61 will cause the speaker 43 to beep with a volume corresponding to the strength or weakness of the detected pulse.

The butterfly patch 40 is placed over the front of the subject's 5 neck 6 so that the left wing 41A is over the left carotid artery 7A and the right wing 41B is over the right carotid artery 7B. The butterfly patch 40 can include an on/off switch 49, or it can be turned on in some other manner, such as removal of the peel-away layer 47, as described above. Alternatively, the butterfly patch 40 could be connected through a port 55 by a conductive cable 74, such as the arrangement shown in FIG. 10 and described below, to a separate display unit 70, which can turn the butterfly patch 40 on or off. Once on, the Doppler transmitters and receivers, 48A and 48B, will begin transmitting ultrasonic signals, 66A and 66B, and receiving their reflections, 67A and 67B. When blood is flowing, the Doppler effect on the reflected signals will be identified by the monitor's 40 circuitry 46, described below, as indicative of the blood's flow velocity, as well as of the frequency of pulses as pulsations of the blood from the heart's pumps is recognized. This rhythmic pulse will be indicated by a blinking light 42 and may further be indicated by an audible sound from a speaker 43.

In a preferred embodiment, the butterfly monitor patch 40 is designed for use with a cervical collar ("C-collar", not shown) around the subject's 5 neck 6, which is common practice in emergency conditions, and in which situations the detection of a pulse is of great importance to medical personnel. To adapt the patch 40 for such use, it should be flat so that a C-collar will fit over the patch 40. Many C-collars include a front opening that exposes the subject's 5 trachea. The light 42, speaker 43, on/off switch 49, and connector port 55 may be located on the middle portion 41C of the butterfly patch 40, so as to be accessible and visible through the C-collar's tracheal opening. If the patch 40 is connected by a cable 74 to a separate unit 70, the cable 74 can reach the patch 40 through the C-collar's tracheal opening.

Figure 8:
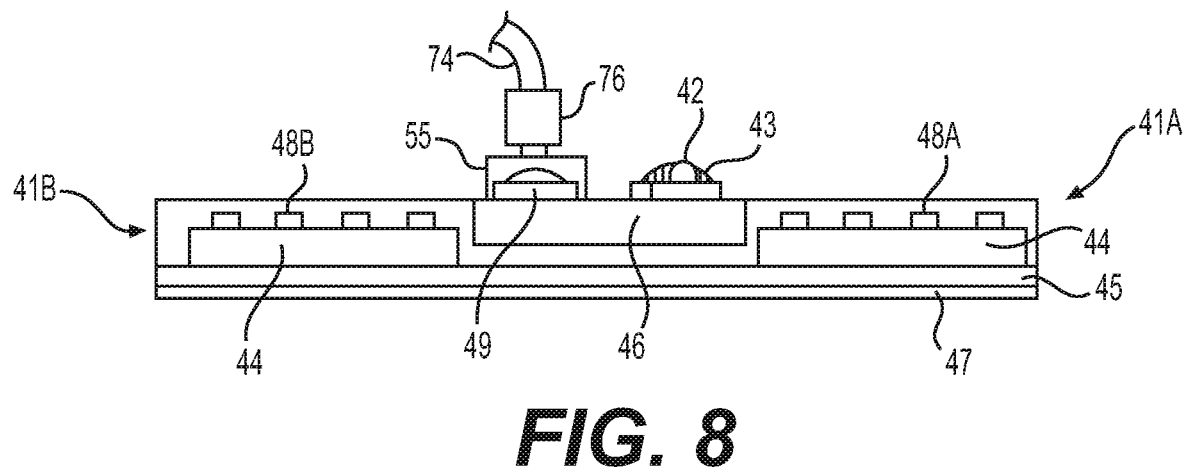
FIG. 8 is a side, cut-away view showing the arrangement of components of the stand-alone pulse-monitoring butterfly patch invention.

FIG. 8 illustrates the parts of the butterfly monitor patch 40. A base 41 supports circuitry 46. Under the base 41 is a conductive pad 44 to enhance transmission and reception of the ultrasonic waves from the circuitry 46 to the patient. As described above, the conductive pad 44 may be a thermoplastic gel or a hydrogel. Hydrogels are hydrophilic networks of polymer chains and may be free-standing or contained within a thin membrane. Beneath the conductive pad 44 is a thin adhesive layer 45 to fix the patch 40 to the subject's 5 skin. A peel-off layer 47 is disposed over the adhesive layer 45 to cover and preserve the adhesive until used. Mounted on the base 41 is the circuitry 46, described below. The circuitry 46 may be mounted on a printed circuit board (PCB), which may be rigid, but, in a preferred embodiment, has some flexibility to conform to the subject's body. The monitor patch 40 may include a light 42, speaker 43, and a switch 49. The switch 49 may turn the patch 40 on or off by activating the circuitry 46, disconnecting power from the power source 68, or the switch 49 may have additional settings. Thus, the switch 49 may turn on the processor 61 and transmitters/receivers, 48A and 48B, and cause the light 42 and speaker 43 to indicate the presence or absence of a pulse, as well as the strength of the pulse, as described above. Or, the switch 49 may have a setting to turn on the light 42 but keep the speaker 43 off, so that the subject's 5 rest is not disturbed. Or, the switch 49 may turn off both the light 42 and the speaker 43 and transmit the pulse data over the cable 74 to a separate display unit 70 (shown in FIG. 10), where the pulse can be indicated by the display unit's 70 light 72A, speaker 73, or graphic display 71. By removing the pulse light and speaker signals from the subject 5 to a remotely located display unit 70, the subject 5 is allowed to rest undisturbed. Similarly, a subject's 5 cardiac status can be monitored at a distance when the subject 5 is not physically near medical personnel, such as when a subject 5 is trapped in a dangerous location or undergoing treatment, such as X-rays or MRI, where medical personnel must remain at a distance.

Figure 9:
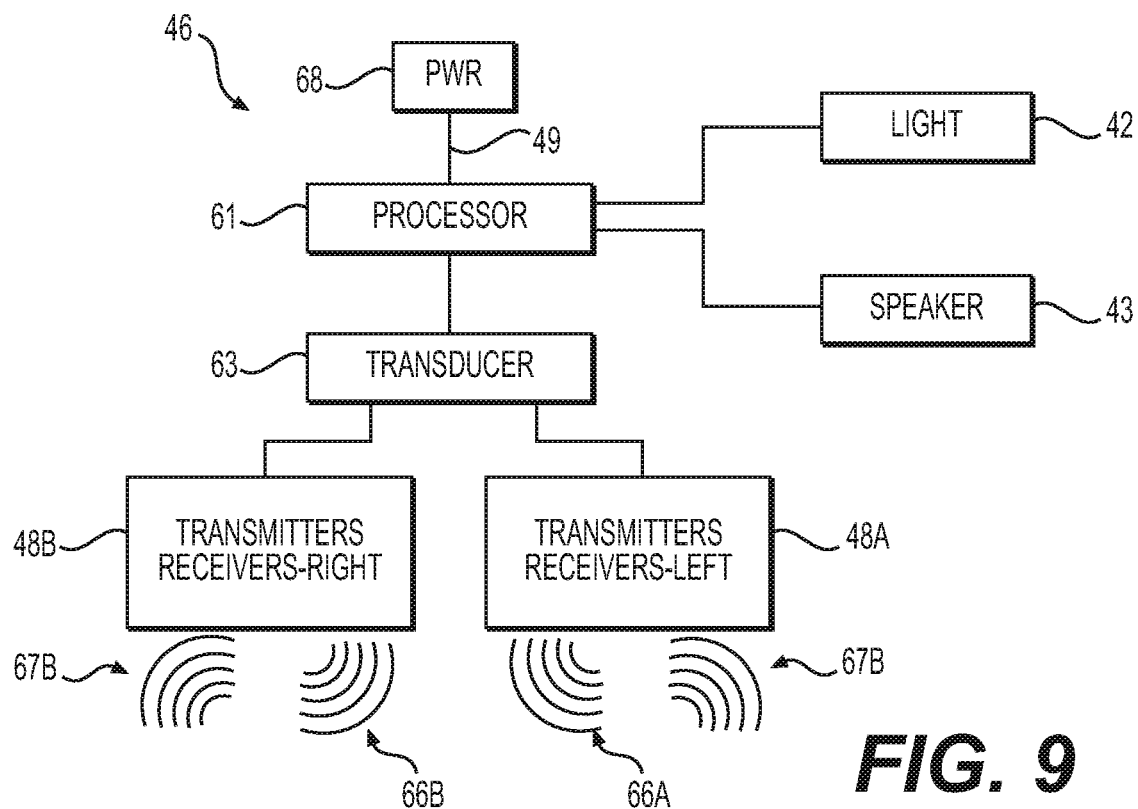
FIG. 9 is a block diagram of the electronic components of the stand-alone pulse-monitoring butterfly patch invention.

FIGS. 8 and 9 show more detail of the circuitry 46 of the butterfly patch monitor 40. A power source 68, such as a small battery, provides integrated power to the electronic components. An on/off switch 49 on the patch 40 can be used to activate the circuitry 46 of the patch 40. As with the previous embodiment, alternative mechanical or electronic switching arrangements may be employed, such as a mechanical switch that activates the circuitry 46 when the peel-away layer 47 is removed. A transducer 63 includes transmitters/receivers, 48A and 48B, arrayed in or over the base 41. The transmitters emit ultrasonic waves, 66A and 66B, and the receivers detect reflected waves, 67A and 67B. The reflected wave signals, 67A and 67B, are demodulated and analyzed by a processor 61, or the transmitted ultrasonic wave signals may be combined with the demodulated reflected wave signals, 67A and 67B, for analysis by the processor 61, to determine whether the reflected wave patterns correspond with Doppler shift signals indicative of flowing blood. Since blood from a heart is pumped in rhythmic pulses, the received Doppler shift signals will indicate that pattern, as described above. Once blood flow is detected, the processor 61 causes a light 42 to blink in synchronization with the rhythm of the heart's pulses. Similarly, the processor 61 will cause a speaker 43 to emit a sound, such as a beep, in synchronization with the rhythm of the heart's pulses. The processor 61 will also analyze the reflected wave signals, 67A and 67B, for their strength by comparing them to known values stored in the processor's 61 memory. Using the stored values, the processor 61 will cause the light 42 to blink with an intensity corresponding to the strength or weakness of the detected pulse. As with the previous embodiment, the light 42 may be a single LED light source capable providing different colors or varying intensities of brightness, or more than one light may be used to accomplish this, and, if no pulse is detected or if a detected pulse fades away, an emergency alarm light, such as a bright red light, may be activated. Similarly, based on the stored values, the processor 61 will cause the speaker 43 to beep in with a volume corresponding to the strength or weakness of the detected pulse and, if no pulse is detected or if a pulse signal fades completely, the processor 61 may cause the speaker 43 to emit a shrill continuous sound.

Figure 10:
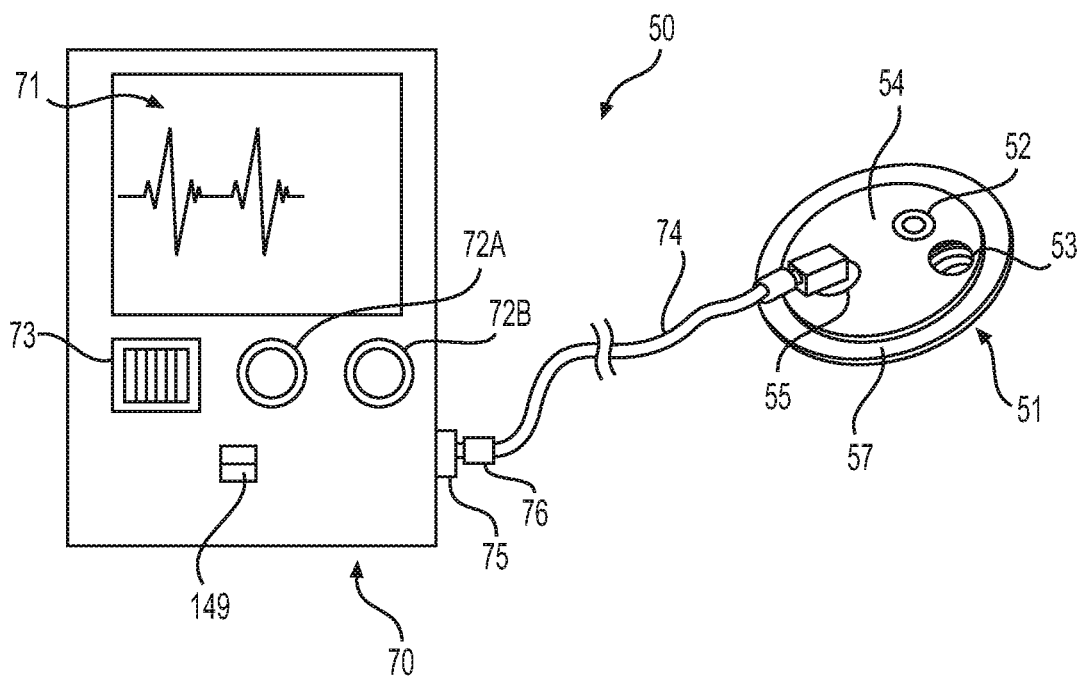
FIG. 10 is a schematic of a stand-alone pulse-monitoring patch connected by a conductive cable to a display unit.
Figure 11:
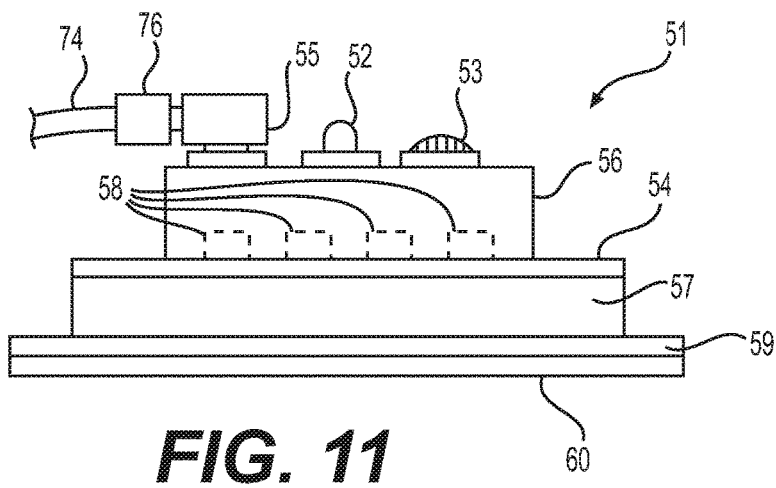
FIG. 11 is a side, cut-away view of a stand-alone pulse-monitoring patch with a connector port for the conductive cable connection.
Figure 12:
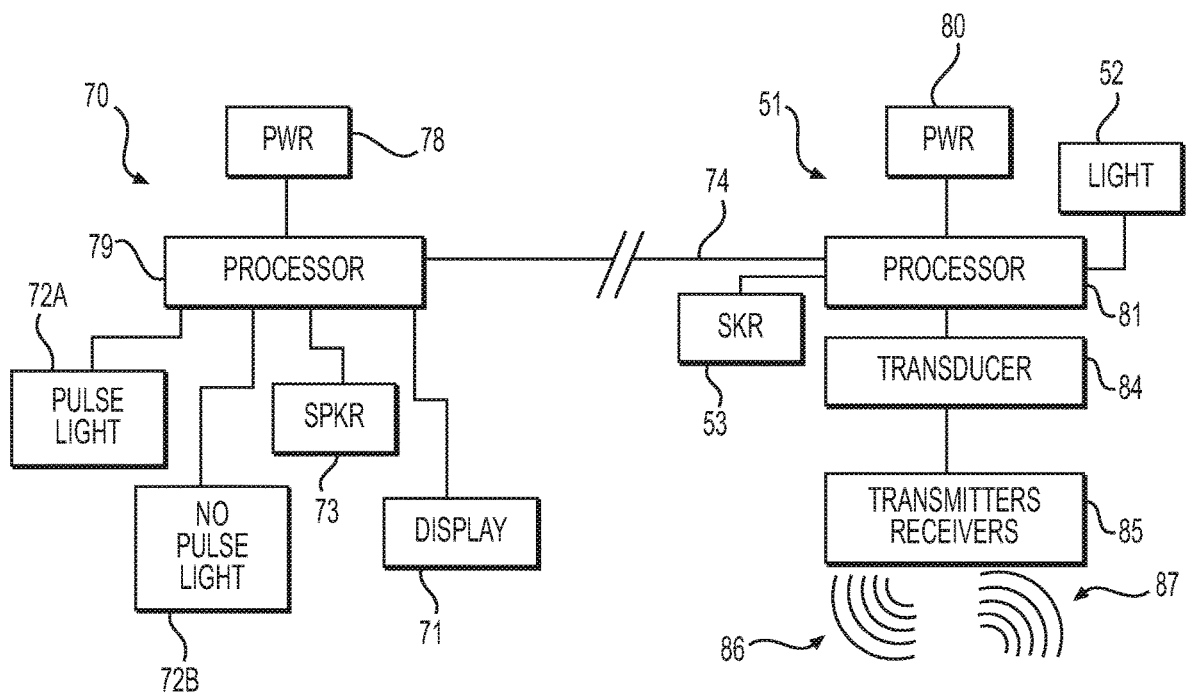
FIG. 12 is a block diagram of the components of a stand-alone pulse-monitoring patch and a display unit connected by a conductive cable.

Referring FIGS. 10 through 12, in an alternative embodiment, a stand-alone continuous cardiac Doppler pulse monitoring patch 51 is connected by one or more conductive data cables 74 to a remote display unit 70. In this embodiment, a patient's blood flow and pulse can be remotely monitored by medical personnel. This capability allows medical personnel to monitor a subject's blood flow remotely when the subject is undergoing procedures, such as X-ray or an MRI, where the light 52 on the patch 51 cannot be seen or the speaker 53 cannot be heard, or when the subject is located in a dangerous area, such as a collapsed building. Also, when a subject is resting, it is possible to turn off the speaker 53 and light 52 on the patch 50 to prevent disturbing the patient, yet continue to monitor the subject's blood flow remotely from the display unit 70. By providing a data cable 74, it is also possible to download data from the memory of the processor 81 of the patch 51. In this way, the patch 51 can store detected cardiac pulse data, which can be downloaded via the data cable 74 to the display unit 70 or a separate computing device and later and analyzed. For example, when emergency medical technicians reach a subject, the stand-alone monitor patch 51 (or the butterfly monitor patch 40 or the wireless monitor patch 90) is activated, applied to the subject, detects a pulse, and the memory in association with the processor 81 begins saving data of the subject's pulse. Later, for example, when the subject reaches hospital, the stand-alone monitor patch 51 (or the butterfly monitor patch 40 or the wireless monitor patch 90) is connected by a data cable 74 to the display unit 70 or a separate computing device and the subject's historical pulse data may be and analyzed to evaluate the heart's behavior from the time the monitor patch was applied.

To accommodate this system 50, the patch 51 includes a port 55 that may receive one or more connectors 76 of one or more conductive cables 74. As noted above, the patch 51 is formed by a base 54, which supports the circuitry 56. The circuitry 56 includes transmitter and receiver units 58 on or incorporated into the base 54. Under the base 54 is a conductive pad 57, as described above. Beneath the conductive pad 57 is a thin adhesive layer 59 to fix the monitor patch 51 to the subject's skin. A peel-off layer 60 is disposed over the adhesive layer 59. Mounted on the base 54 is the circuitry 56, described below. The circuitry 56 may be mounted on a printed circuit board (PCB), which may be rigid, but, in a preferred embodiment, has some flexibility to conform to the subject's body. Over the circuitry 56 are one or more lights 52 and a speaker 53 and, in some embodiments, a manual on/off switch may be included, such as has been described above. The port 55 shown in FIGS. 10 and 11 is directed to receive a connector 76 from the side, along the plane of the base 54, which is a preferred orientation when the patch 51 is placed over one of the subject's carotid artery, so that the cable 74 will not project away from the neck, which could interfere with a C-collar or present an obstruction to the subject and medical personnel. In contrast, the butterfly monitor patch 40 shown in FIGS. 5 through 9 has a connector port 55 in the middle portion 41C directed to receive the connector 76 from above, normal to the plane of the base 41, which places the light 42, speaker 43, switch 49, connector port 55, and cable 74 within the tracheal opening provided in many cervical collars. The embodiments shown have a single port 55, connector 76 and cable 74, but multiple ports and cable connectors could be accommodated.

The cable 74 connects to the remote display unit 70 through a port 75. The cable 74 may be permanently connected to the display unit 70 or the cable may have a connector 76 so that it may be disconnected. In the embodiment shown in FIG. 10, the display unit 70 has two lights, 72A and 72B, so that the heart rhythm and flow strength can be indicated on one light or light cluster 72A and an emergency light indicator 72B can show that the subject's heart has stopped pumping blood or is dangerously close to doing so. The display unit 70 also has a speaker 73 to provide an audible indicator the subject's heart rhythm and strength, and the speaker may also provide an emergency sound to indicate that the subject's heart is or has failed. The unit 70 may also include a graphic display screen 71 to provide textual, numerical and graphical information about the subject's blood flow, such as a numerical display of heart rate (bpm) and blood velocity (cm/s), as well as a waveform to show the strength of the subject's pulse, pressure, and blood velocity over time. A switch 149 is provided to turn the display unit 70 on or off.

Referring to FIGS. 11 and 12, in one embodiment, the stand-alone monitor patch 51 has its own power source 80, such as a small battery, to provide integrated power to the electronic components. A switch, as in previously disclosed embodiments may also be incorporated into the patch 51. A transducer 84 includes transmitters/receivers 85 (shown as units 58 in FIG. 12) arrayed in or over the base 54. The transmitters emit ultrasonic waves 86 and the receivers detect reflected waves 87. As described above, the reflected wave signals 87 are demodulated and analyzed by a processor 81 to determine whether the reflected wave pattern corresponds with Doppler shift signals indicative of flowing blood. Once a blood flow is detected, the processor 81 causes the light 52 to blink in synchronization with the rhythm of the heart's pulses. Similarly, the processor 81 will cause a speaker 53 to emit a sound, a beep, in synchronization with the rhythm of the heart's pulses. The processor 81 will also analyze the reflected wave signals 87 for their strength by comparing them to known values stored in the processor's 81 memory. Using the stored values, the processor 81 will cause the light or lights 52 to blink with an intensity corresponding to the strength or weakness of the detected pulse. Similarly, based on the stored values, the processor 81 will cause the speaker 53 to beep in with a volume corresponding to the strength or weakness of the detected pulse.

The patch 51 is connected to the display unit 70 by cable 74, as previously disclosed. The display unit 70 has its own power source 78 to power its components. The display unit's 70 processor 79 receives the heart flow and velocity data from the patch 51 and causes one or more lights 72A to display the pulse in the manner described above, A no-pulse light 72B can provide a visual signal that the subject's pulse has failed. A speaker 73 can emit sounds to provide audible signals of the subject's pulse. A display 71 provides textual, numerical and graphical information about the subject's blood flow, such as a numerical display of pulse rate (bpm)

and blood velocity (cm/s), as well as a waveform to show the strength of the subject's pulse, pressure, and blood velocity over time. The processor's 79 memory can store data of the subject's cardiac status over time by downloading such data from the stand-alone monitor patch 51 processor's 81 memory and from the display unit's 70 processor's 79 memory, and this historical data may be displayed on the unit's 70 screen 71 or transmitted to other medical equipment for analysis.

Figure 13:
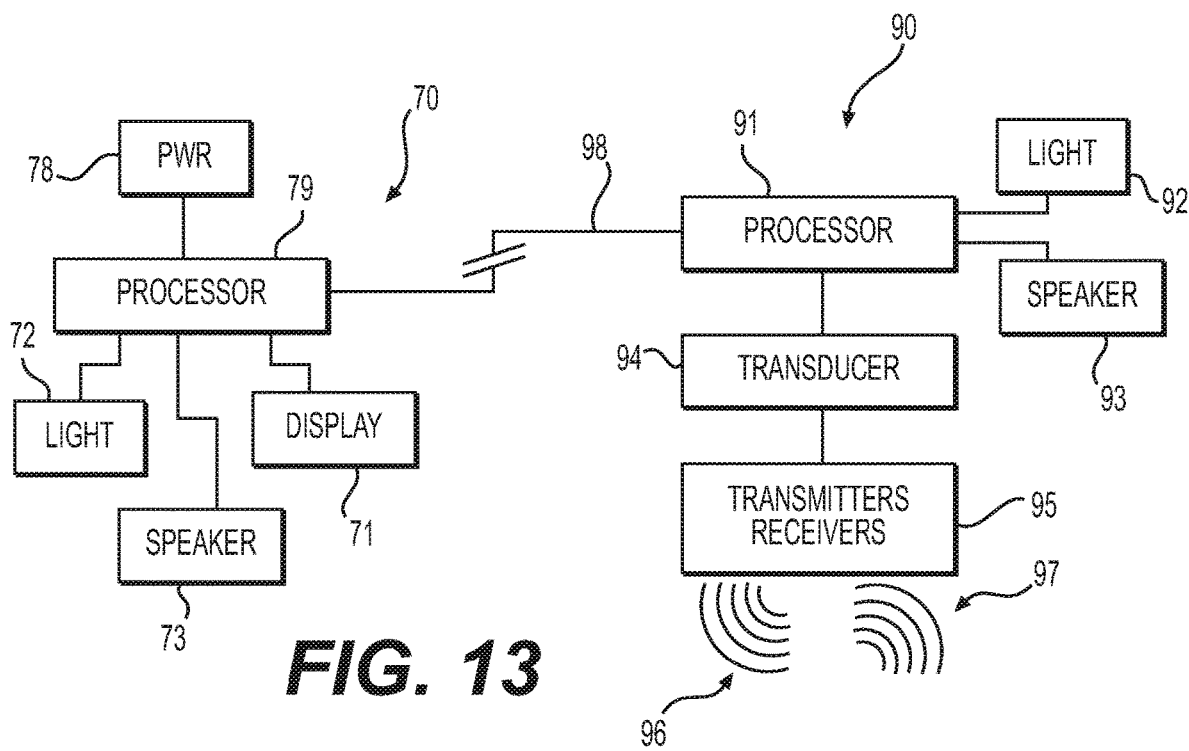
FIG. 13 is a block diagram of the components of an alternate embodiment of a patch connected by a conductive cable to a display unit.

Referring to FIG. 13, an alternative embodiment is disclosed whereby a remote display unit 70 includes a power source 78 to provide power to a monitor patch 90 over a power and data cable 98 to power the patch components, such as the processor 91, transducer 94, transmitters/receivers 95, light(s) 92, and speaker 93. The display unit 70 is a compact, hand-held box, capable of accommodating more battery power, processing, and memory, and display options than the patch 90 can provide. In a basic embodiment, the unit 70 is very compact and includes only one indicator of the subject's blood flow, such as the light 72.

Figure 14:
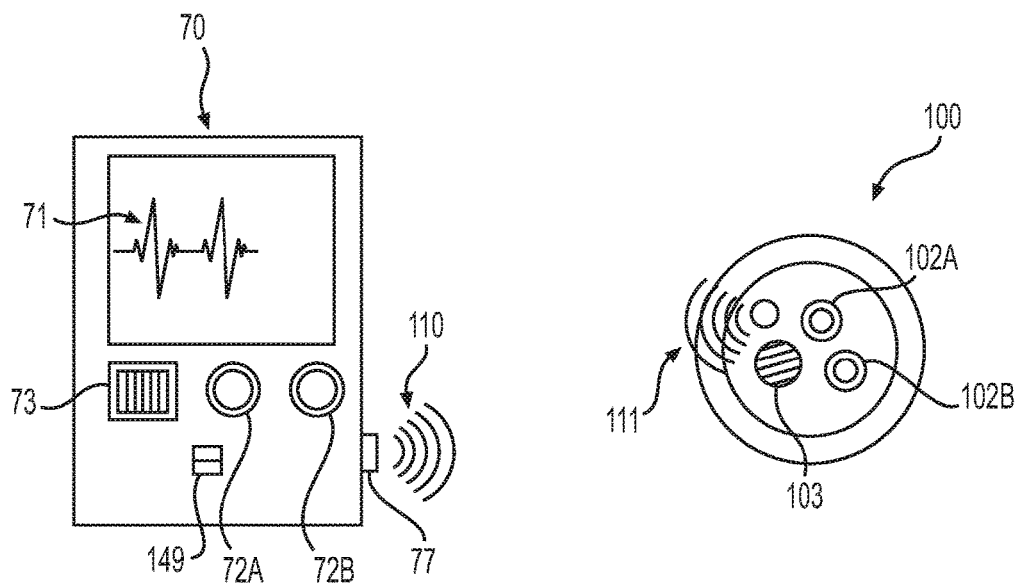
FIG. 14 is a schematic of a simplified pulse-monitoring patch connected wirelessly to a display unit.
Figure 15:
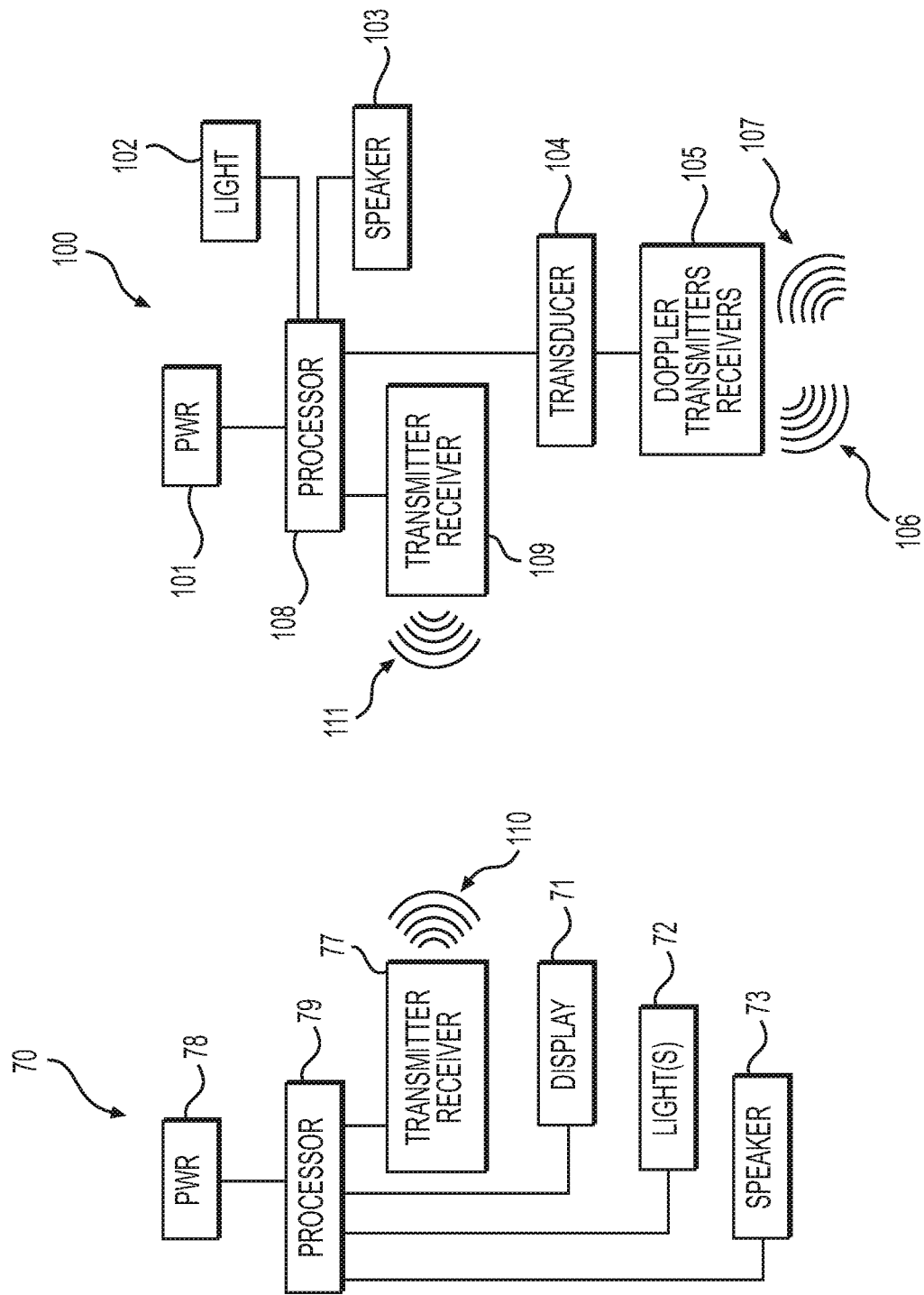
FIG. 15 is a block diagram of the components of an alternate embodiment of a patch and a display unit connected wirelessly.

Referring to FIGS. 14 and 15, an alternative embodiment is disclosed whereby the stand-alone monitor patch 100 transmits and receives 111 wireless data signals from the remote display unit 70. In this embodiment, the patch 100 includes its own power source 101 and transmitter/receiver 109. The display unit 70 also has a transmitter/receiver 77 to receive and send data to the patch 50.

Figure 16:
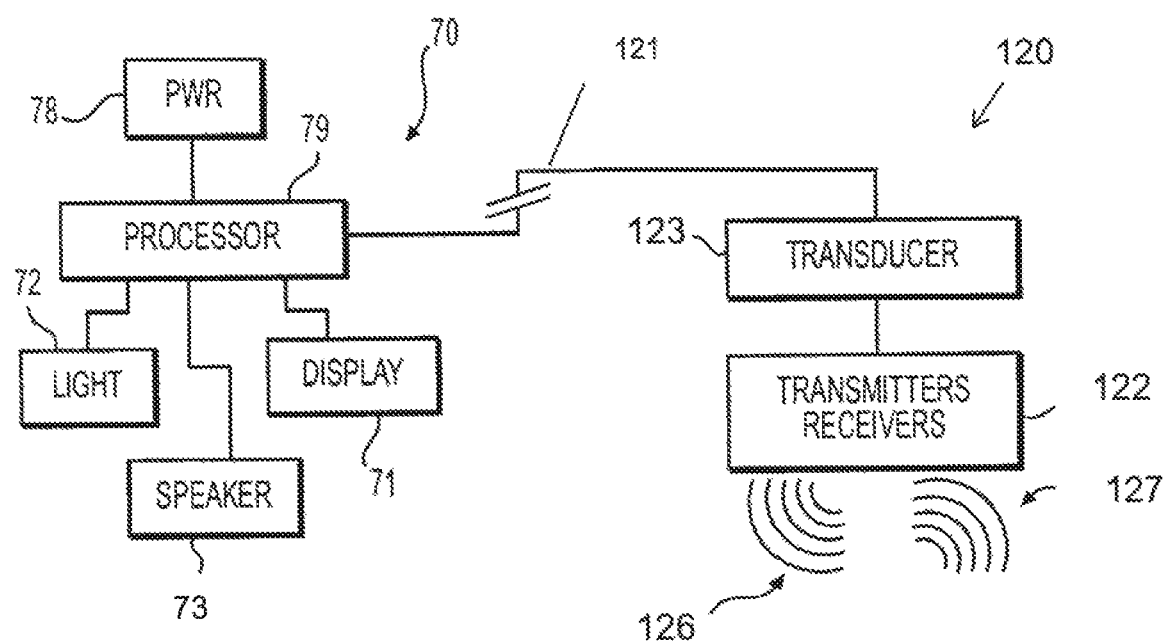
FIG. 16 is a block diagram of the components of an alternate embodiment of a simplified patch and a display unit system.

Referring to FIG. 16, another alternative embodiment is disclosed whereby the display unit 70 provides power from a power source 78 and processing from a processor 79 via a power and data cable 121 to a simplified monitor patch 120 to power the transducer 123 and transmitters/receivers 122, which operate as described above. The simplified monitor patch 120 is less expensive to make, since it has fewer components, and may discarded after use, while the display unit 70 may be re-used.

Figure 17:
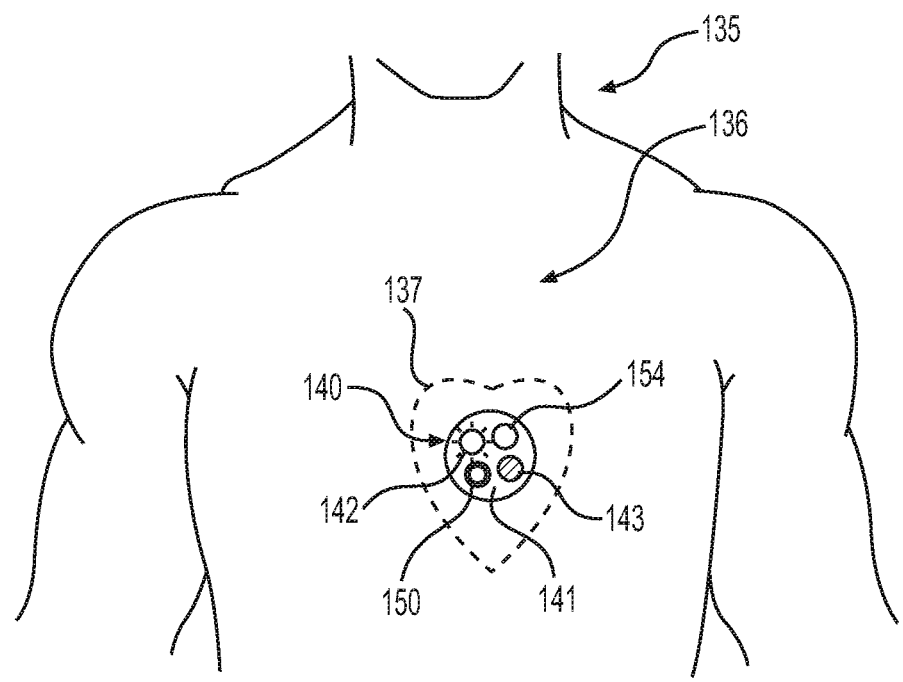
FIG. 17 shows a stand-alone continuous cardiac acoustic pulse-monitoring patch with visual and auditory alerts of the present invention applied to the chest of a patient.
Figure 18:
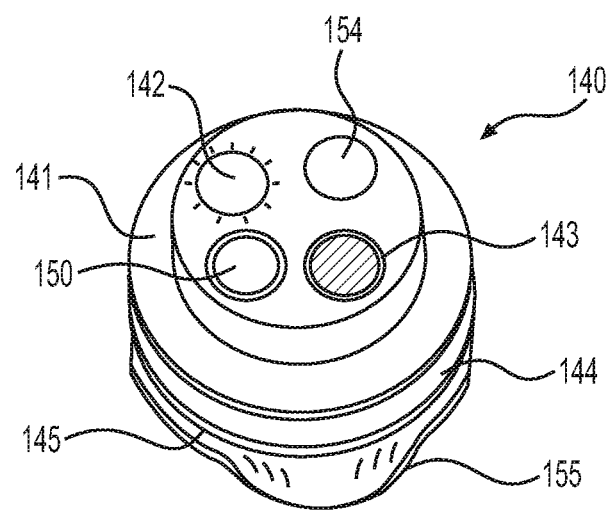
FIG. 18 is a side view showing the layers the stand-alone acoustic pulse-monitoring patch.

FIGS. 17 through 20 show the stand-alone continuous acoustic heart monitor patch 140. FIG. 17 shows the acoustic monitor patch 140 applied to the chest 136 of a patient 135 over the patient's 135 heart 137. In this position, the acoustic monitor 140 will be in the best position to detect the sound (157 shown in FIG. 20) of a beating heart 137. The chest 136 over a subject's 135 heart 137 is best position from which to detect a heartbeat, since it is in the closest distance to the heart 137 and provides a direct path through which the sound 157 of the heartbeat may travel. The acoustic monitor 140 may be placed over arteries, such as the carotid, femoral or radial arteries, in order to listen for heartbeats 157 while CPR is being applied to the chest 136 or when other procedures require access to the chest 136. The acoustic monitor 140 is secured on the subject's 135 chest 136 over the heart 137 by removing the peel-away layer 147 to expose the adhesive 145 (shown in FIG. 19). A tab 155 extending out from the edge of the peel-away layer 147 can be gripped easily to facilitate removal. The on/off switch 150 is turned to the on position and the acoustic monitor's 140 microphone 148 (shown in FIG. 19) will begin listening for a heartbeat. When blood is being pumped by the heart 137, the heartbeat will be heard, along with other sounds, by the acoustic monitor's 140 microphone 148. The sounds 157 are received by a microphone 148 and the energy of the sound is transmitted to a transducer 153. The sound energy from the microphone 148 may be pre-filtered (156 in FIG. 20) to remove sounds are outside the desired range for detection. The sounds may also be amplified so that increase the acoustic signals to a range for which the full resolution of the acoustic monitor patch 140 is designed to analyze. The transducer 153 includes an analog-to-digital (A-to-D) converter that converts the analog acoustic signals into digital signals. The digital signals are sent to the digital signal processor (DSP) 153. The processor 153 has integrated memory and software that allows digital filtering of the signals to eliminate as much unwanted noise as possible by identifying and removing digital signals outside the range targeted for detection. The processor 153 may use a field programmable gate array (FPGA) to detect targeted acoustic signal data in order to extract information about known sound patterns. The processor 153 compares the digital signal patterns with heartbeat models stored in the processor's 153 memory to distinguish the sounds associated with a heartbeat from other sounds. For example, the heartbeat signals 157 can be compared to known signal patterns of a normal heartbeat as well as patterns associated with known abnormal heartbeats (arrhythmia), such as premature atrial or ventricular contractions, atrial fibrillation or flutter, paroxysmal supraventricular or accessory pathway tachycardia, ventricular tachycardia or fibrillation, bradyarrhythmias, etc. The processor 153 determines the frequency and strength of the heartbeat and causes a light 142 on the upper surface of the acoustic monitor patch 140 to blink in time with the frequency of the heartbeat. The intensity of the light 142 may be varied to indicate the strength or weakness of the heartbeat. This rhythmic blinking of the light 142 may further be indicated by an audible sound, such as a beep, from a speaker 143. Additionally, the monitor patch 140 may include a vibrator 154, such as a pancake vibration motor, to provide a sensory indicator the rhythm and strength of the heartbeat. By placing a finger on the monitor patch 140, the subject's 135 heartbeat can be felt through the vibrator 154 when surrounding conditions make seeing the light 142 or hearing the speaker 143 difficult, as in a fire, where smoky and noisy conditions may make other indicators difficult to detect.

Figure 19:
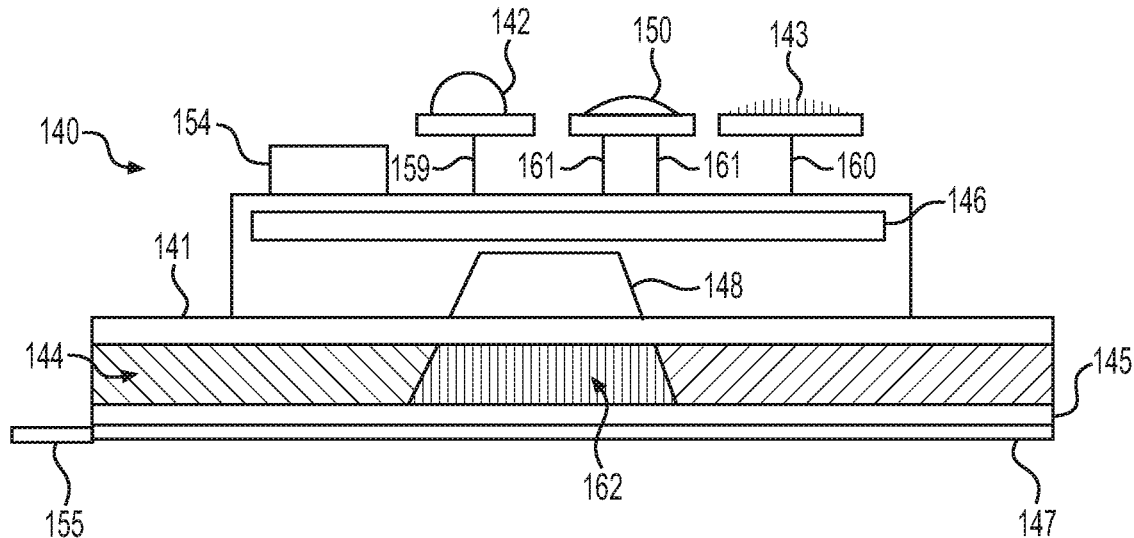
FIG. 19 is a side, cut-away view showing the arrangement of components of the stand-alone acoustic pulse-monitoring patch invention.

FIG. 19 illustrates the parts of the acoustic monitor patch 140. The bottom of the monitor patch 140 is formed by a base 141, which supports the circuitry 146. Under the base 141 is an acoustic pad 144 to focus the incoming sounds of a heartbeat 157 and insulate the microphone 148 from surrounding noise. The acoustic pad 144 may be a thermoplastic gel or a hydrogel, as discussed above. The density of the acoustic pad 144 may be varied to allow more sound to pass directly in front 162 of the microphone 148 while providing more sound insulation at the periphery. Beneath the conductive pad 144 is a thin adhesive layer 145 to fix the monitor patch 140 to the subject's skin. A peel-off layer 147 is disposed over the adhesive layer 145 to cover and preserve the adhesive until used. A tab 155 extending from the outer edge of the peel-away layer 147 and the base 141, facilitates removing the adhesive layer 145. Mounted on the base 141 is the circuitry 146, described below. The circuitry 146 may be mounted on a printed circuit board (PCB), which may be rigid, but, in a preferred embodiment, has some flexibility to conform to the subject's body contours. Over the circuitry 146 is a light 142 to indicate the strength and frequency of the detected heartbeat. The acoustic monitor patch 140 may also include a speaker 143, vibrator 154, and manual on/off switch 150. A conductor 161 from the circuitry 146 to the light 142 allows electricity to flow to the light 142. Similarly, a conductor 160 controls electrical flow to the speaker 143, a conductor (not shown) controls electrical flow from the circuitry 146 to the vibrator 154, and conductors 161 provide connectivity between the on/off switch 150 on the circuitry 146.

Figure 20:
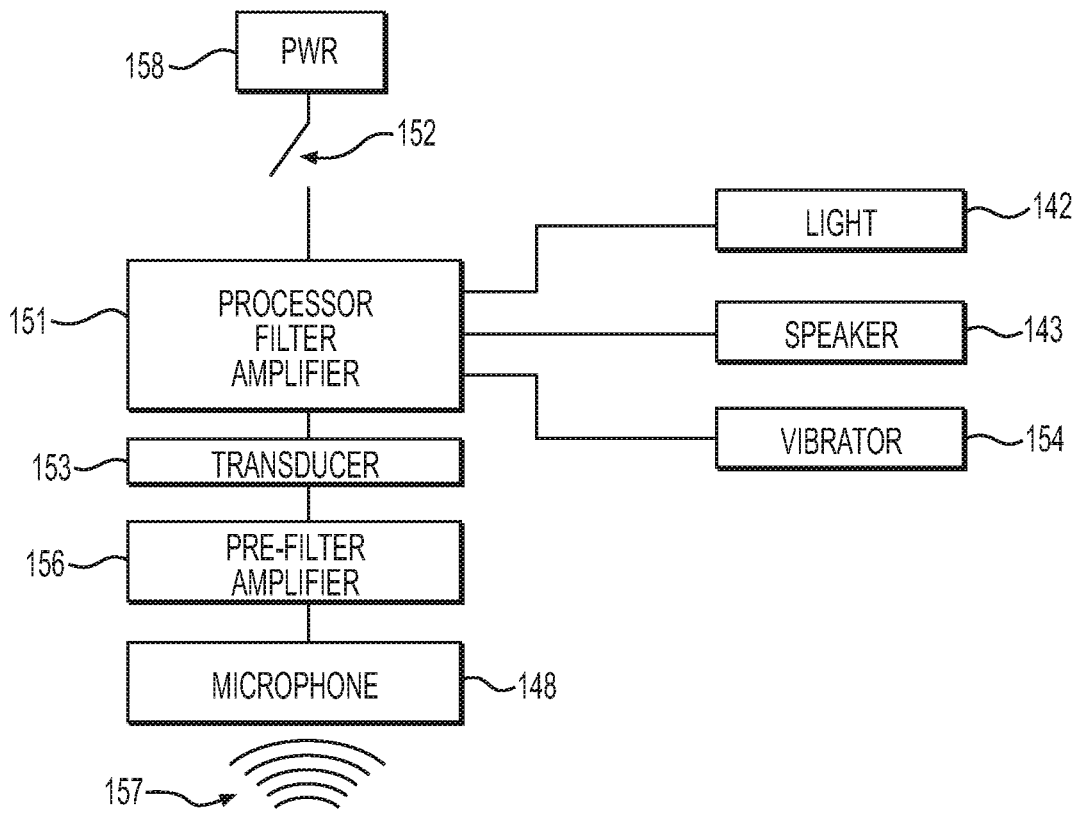
FIG. 20 is a block diagram of the electronic circuitry of the stand-alone acoustic pulse-monitoring patch invention.

FIG. 20 shows more detail of the circuitry 146. A power source 158, such as a small battery, provides integrated power to the electronic components of the stand-alone monitor patch 140. A switch 152 controls power or can activate the circuitry 146 from a low-power consumption rest state. A microphone 148 receives the mechanical sound energy of a heartbeat 157. A transducer 153 receives the electrical signals from the microphone 148. In a preferred embodiment, the electrical signals from the microphone are prefiltered and amplified 156. The transducer 153 converts the analog acoustic signals into digital signals and the digital signals are sent to the processor 153. The processor 153 processes the digital signal to filter out unwanted noise, identify the presence or absence of sounds associated with a heartbeat 157, and analyze the digital heartbeat data for frequency, strength, and arrhythmia patterns, as discussed above. Once the sound of a heartbeat is detected, the processor 151 causes the light 142 to blink in synchronization with the rhythm of the heartbeat. Similarly, the processor 151 may cause a speaker 143 to emit a sound, such as a beep, in synchronization with the rhythm of the heartbeat, and a vibrator 154 may vibrate in synchronization with the heartbeat to provide an indicator of the heartbeat that be detected by touch. The processor 151 will also analyze the acoustic signals 157 for known symptoms stored in the processor's 151 memory. Using the stored values, the processor 151 will cause the light 142 to blink with an intensity corresponding to the strength or weakness of the detected pulse. Similarly, based on the stored values, the processor 151 will cause the speaker 143 to beep with a volume corresponding to the strength or weakness of the detected pulse. Additionally, based on the stored values, the processor 151 will cause the vibrator 154 to vibrate with a rhythm and strength or weakness indicative of the detected heartbeat.

The light 142 may be an LED. In a preferred embodiment, the LED light 142 is capable of emitting different colors of light, such as red and green. For example, if a healthy pulse is detected by the monitor patch 140, the processor 151 will cause the light 142 to blink with a green color indicating a healthy pulse, but if a weak pulse is detected, the processor 151 will cause the light 142 to emit a yellow or red color. Alternatively, two or more lights 142 may be employed to indicate strength (i.e., more lights indicate a stronger heartbeat and fewer lights a weaker), or each LED is chosen to emit a different color. As described above, the processor 151, relying on values stored in the processor's memory, will cause the intensity of the light to increase or decrease, or the color of the light to change, in relation to the strength or weakness of the detected heartbeat. Similarly, the processor 151 will cause the speaker 143 to increase or decrease the volume, or change another characteristic of the emitted sound in relation to the strength or weakness of the detected heartbeat. Additionally, the vibrator 154 will cause the acoustic monitor patch 140 to vibrate with increasing or decreasing intensity in relation to the strength or weakness of the detected heartbeat. If the processor 151 detects a weak or declining pulse, the processor 151 will cause a color-changing LED light 142 to change in color, for example from green to red, or will shift the visual indicator from one color (e.g., green) light to a different color (e.g., yellow or red) light. Similarly, the processor 151 may cause the speaker 143 to emit a different sound as a weak or declining pulse is detected. Additionally, the processor 151 may cause the vibrator 154 to vibrate more rapidly as a weak or declining pulse is detected. If a heartbeat is lost, the processor 151 can cause a color-changing LED light 142, or a separate light, to emit a continuous bright, emergency red light. Similarly, if no heartbeat is detected or if a heartbeat signal fades completely, the processor 151 may cause the speaker 143 to emit a shrill continuous emergency sound.

In operation, the continuous cardiac acoustic monitor patch 140 will be applied to a patient 135 when a continuous pulse needs to be identified. The acoustic monitor patch 140 is activated or turned on by a switch 150, the peel-off layer 147 is removed, exposing the adhesive 145, and the monitor patch 140 is placed on a subject's 135 chest 136 over the heart 137. It will be appreciated that the sequence of activating the switch 150 and removing the peel-off layer 147 may be reversed. In an alternative embodiment, the removal of the peel-off layer 147 will turn on or activate the circuitry 146 of the monitor patch 140, either by turning a switch 150 to the active "on" position or by closing the on/off circuit 152 to the power source 158. By deactivating the circuitry 146 of the monitor patch 140, or cutting off power from the power source 158, the switch 150 allows the monitor patch 140 to be inactive for long periods of time, such as during storage, yet be available in an instant when needed. When the monitor patch 140 is turned on, the processor 151 will direct the transducer 153 to send and receive acoustic signals 157 from the microphone 148. The acoustic signals 157 are analyzed by the processor 151 and compared to values stored in the processor's 151 memory. If the heartbeat signals 157 correspond to a stored value for a heartbeat, the processor 151 will cause the light 142 to blink in synchronization with the heartbeat and with an intensity corresponding to the strength or weakness of the heartbeat. Similarly, the processor 151 will cause the speaker 143 to beep in synchronization with the heartbeat and with a volume corresponding to the strength or weakness of the heartbeat. Additionally, the processor 151 will cause the vibrator 154 to vibrate in synchronization with the heartbeat.

The acoustic monitor patch 140 may be used on unstable patients or patients with the potential of instability. Identifying the absence of a heartbeat is paramount to initiating CPR. The monitor patch 140 can also be applied while patients 135 are in motion. For example, moving patients 135 down stairs or transporting patients 135 in a helicopter. Moving patients 135 downstairs requires that the transporting personnel be at the head and foot of the stretcher, where they are unable to verify a continuous heartbeat. Similarly, air medical evacuations, and even automotive transportation, are loud and vibrations distracting, interfering with the detection of a heartbeat. For example, it is difficult to auscultate a heartbeat in a helicopter. The acoustic monitor patch 140 uses a light 142 as proof of a heartbeat. Moreover, in low visibility environments, the acoustic monitor patch 140 uses a speaker 143 as proof of a heartbeat. Additionally, in situations involving low visibility and loud ambient noise, where the light 142 and speaker 143 may be difficult to detect, such as in fires or battlefields, the vibrator 154 provides another means to detect the presence or absence of a heartbeat in a subject 135.

The acoustic monitor patch 140 will, preferably, be placed on a subject's 135 chest 136 over the heart 137. In situations where this is impeded, the acoustic monitor patch 140 may be placed over a large artery 6 (as in FIG. 1), such as the carotid, radial, or femoral arteries.

The acoustic monitor patch 140 of the present invention is designed as a stand-alone that integrates the switch 150, light 142, speaker 143, vibrator 154, circuitry 146, base 141, conductive pad 144, and adhesive layer 145 into a unitary and compact device configured to conform and adhere to the contours of a subject's 135 skin above the heart 137. Ideally, a small patch of about 2½ inches in diameter, or about 5 square inches, will conform easily to the contours of the patient's skin and reside over an area where a heartbeat may be detected. Stand-alone acoustic monitor patches of the invention may be larger to provide more space for circuitry and cover greater area over the heart 137 or an artery 6; such stand-alone acoustic monitor patches 140 are not limited in size, but a larger patch will be cumbersome and difficult to apply. It is preferred, but not required that stand-alone acoustic monitor patches cover areas of less than about twenty square inches.

The monitor patch 140 will be able to generate visual 142, auditory 143 and sensory 154 signals. The signal will increase and decrease in intensity based on the strength of the heartbeat. This enables the medical provider to determine if the patient's 135 heartbeat is strong, weak, or absent. The signals (light & sound) also vary in intensity with a diminishing or increased heartbeat. This enables the medical provider to determine if a heartbeat is weakening or stopping and the provider will be able to take appropriate actions and determine if a treatment is working by an increased heartbeat signal.

The acoustic monitor patch 140 of the present invention can monitor dynamic changes in unstable or potentially unstable patients. With this information the medical provider can use the intensity of the light/sound signal to closely follow the heartbeat and mange therapy in real time. This feature is especially helpful in evaluating the effectiveness of CPR. A strong signal will signify adequate CPR, improving success to Return of Spontaneous Circulation (ROSC).

The invention also provides a simple continuous cardiac acoustic monitor patch 140 for checking fetal distress in pregnancy.

The acoustic monitor patch 140 of the present invention can also monitor a subject's 135 breathing and provide visual 142, auditory 143, and sensory 154 indicators of symptoms of distress. As with the acoustic cardiac monitoring described above, the speaker 148 can also detect sounds associated with the subject's 135 breathing. The processor 151 receives the breathing sounds from the transducer 153 and compares the received sounds to known breathing patterns stored in the processor's 151 memory. For example, sounds associated with shallow breathing may indicate an overdose state from substances such as opiates or alcohol. Also, in listening for the subject's 135 breathing, the acoustic monitor patch 140 may not detect any sound associated with known patterns of breathing. In such events, the processor 151 of the acoustic monitor patch 140 can cause the light 142, speaker 143, or vibrator 154 to emit distinct signals associated with respiratory distress.

Figure 21:
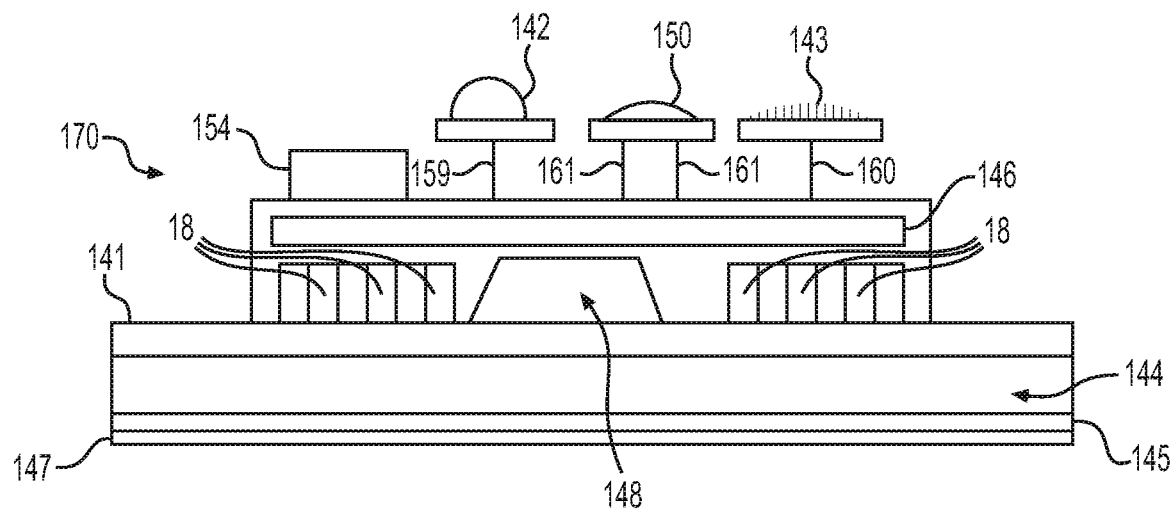
FIG. 21 is a side, cut-away view showing the arrangement of components of the stand-alone combined Doppler and acoustic pulse-monitoring patch invention.
Figure 22:
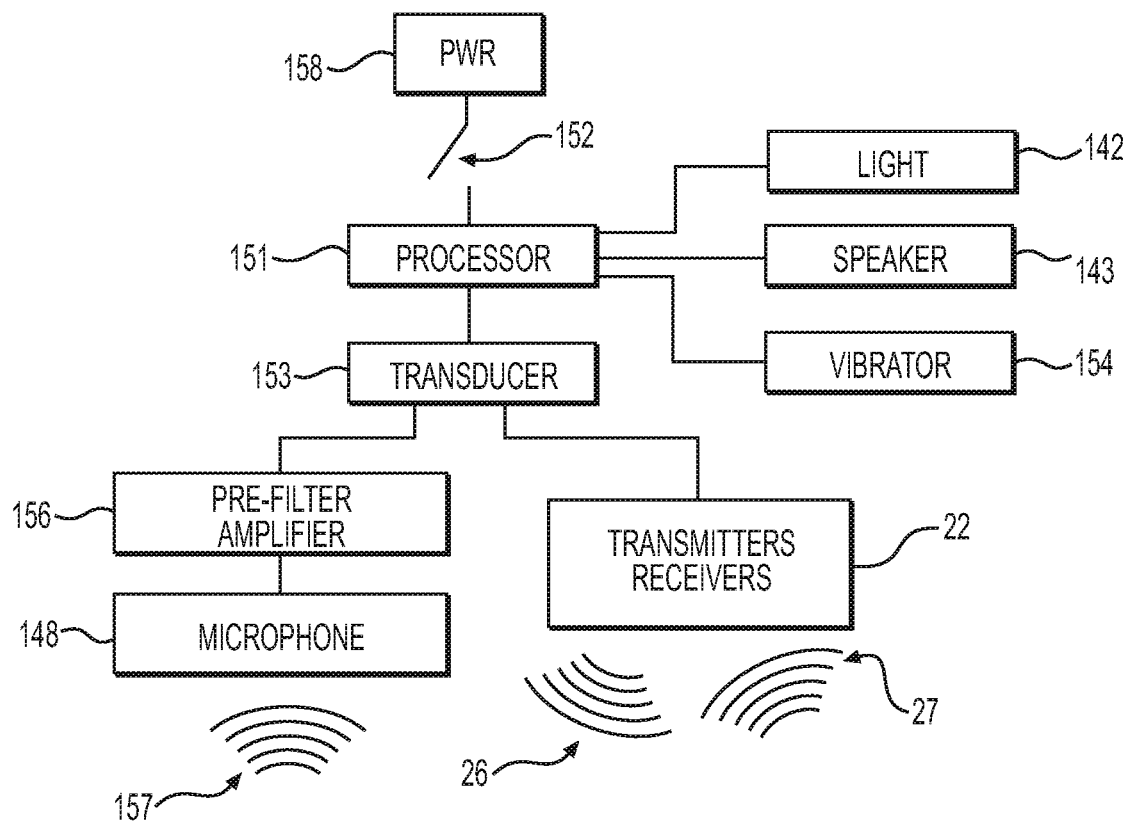
FIG. 22 is a block diagram of the electronic circuitry of the stand-alone combined Doppler and acoustic pulse-monitoring patch invention.

FIGS. 21 and 22 show the stand-alone continuous combined acoustic and Doppler heart monitor patch 170. As described in connection with the acoustic monitor patch 140 shown in FIG. 21, the acoustic/Doppler monitor patch is 170 applied to the chest 136 of a patient 135 over the patient's 135 heart 137. In this position, the acoustic/Doppler monitor 140 will be in the best position to detect the sound of a beating heart 137 and the flow of blood through the heart 137.

FIG. 22 illustrates the parts of the combined acoustic/Doppler monitor patch 170. The bottom of the monitor patch 140 is formed by a base 141, which supports the circuitry 146. Under the base 141 is an acoustic pad 144 to focus the incoming sounds of a heartbeat 157, insulate the microphone 148 from surrounding noise, and enhance transmission and reception of the ultrasonic waves, 26 and 27, from and to the circuitry 146 to the patient 135, as discussed above. Beneath the conductive pad 144 is a thin adhesive layer 145 to fix the monitor patch 140 to the subject's skin, as discussed above. Mounted on the base 141 is the circuitry 146, as described above. Over the circuitry 146 is a light 142 to indicate the strength and frequency of the detected heartbeat and pulse, as discussed above.

FIG. 22 shows more detail of the circuitry 146. A power source 158 provides integrated power to the electronic components of the stand-alone acoustic/Doppler monitor patch 170. A switch 152 controls power or can activate the circuitry 146 from a low-power consumption rest state. A microphone 148 receives the mechanical sound energy of a heartbeat 157. Transmitters and receivers 22 are arrayed in or over the base 141. The transmitters emit ultrasonic waves 26 and the receivers detect reflected waves 27. The transducer 153 receives the electrical signals from the microphone 148 and the transmitter/receiver 22. The reflected wave signals 27 are demodulated and analyzed by the processor 151 to determine whether the reflected wave pattern corresponds with Doppler shift signals indicative of flowing blood. In a preferred embodiment, the electrical signals from the microphone are prefiltered and amplified 156. The transducer 153 converts the analog acoustic signals into digital signals and the digital signals are sent to the processor 153. The processor 153 processes the digital signal to filter out unwanted noise, identify the presence or absence of sounds associated with a heartbeat 157. The processor 151 analyzes the digital heartbeat and pulse data from the microphone 148 and transmitter/receiver 22 for frequency, strength, and arrhythmia patterns, as discussed above. Once the sound of a heartbeat and pulse are detected, the processor 151 causes the light 142 to blink in synchronization with the rhythm of the heartbeat, as discussed above. Similarly, the processor 151 may cause a speaker 143 to emit a sound, such as a beep, in synchronization with the rhythm of the heartbeat and pulse, and a vibrator 154 may vibrate in synchronization with the heartbeat and pulse to provide an indicator of the heartbeat that be detected by touch. The processor 151 will also analyze the acoustic signals 157 as well as the pulse signals for known symptoms stored in the processor's 151 memory. Using the stored values, the processor 151 will cause the light 142 to blink with an intensity corresponding to the strength or weakness of the detected heartbeat and pulse. Similarly, based on the stored values, the processor 151 will cause the speaker 143 to beep with a volume corresponding to the strength or weakness of the detected heartbeat and pulse. Additionally, based on the stored values, the processor 151 will cause the vibrator 154 to vibrate with a rhythm and strength or weakness indicative of the detected heartbeat and pulse.

The drawings and description set forth here represent only some embodiments of the invention. After considering these, skilled persons will understand that there are many ways to make a continuous Doppler cardiac pulse monitor patch according to the principles disclosed. The inventor contemplates that the use of alternative structures, materials, or manufacturing techniques, which result in a monitor patch according to the principles disclosed, will be within the scope of the invention.

The invention claimed is:

1. A stand-alone continuous acoustic heart monitor patch comprising:
    a base having an upper base surface and a lower base surface on a side opposite the upper base surface,
    circuitry disposed on the upper base surface, the circuitry comprising at least one microphone configured to receive sounds, an analog to digital converter for converting the sounds from the microphone to digital audio signals and delivering the digital audio signals to a processor, a power source providing power to the circuitry, and memory in association with the processor, wherein the processor processes the digital audio signals, a pad having an upper pad surface and a lower pad surface opposite to the upper pad surface, wherein the upper pad surface is disposed on the lower base surface, wherein the pad further comprises a sound focusing area between the upper pad surface and the lower pad surface, wherein the sound focusing area is disposed proximate the microphone, wherein the pad further comprises a sound insulating area between the upper pad surface and the lower pad surface and surrounding the sound focusing area, an adhesive layer having an upper adhesive surface and a lower adhesive surface opposite the upper adhesive surface, wherein the upper adhesive surface is disposed on the lower pad surface, and wherein the lower adhesive surface is adapted to adhere releaseably to skin of a human, a peel-away sheet disposed on the lower adhesive surface, wherein the peel-away sheet is removable from the lower adhesive surface to expose the lower adhesive surface, and wherein the patch is adapted and to conform to a contour of the skin of a chest over a heart and the patch is sized to fit on the skin over a portion of the heart, wherein the processor is adapted to detect a heartbeat or an absence of a heartbeat from the sounds received by the microphone, wherein the processor causes a heartbeat signal to be emitted indicative of the detected heartbeat, and wherein the base, circuitry, pad, adhesive layer, and peel-away sheet are integrated into the patch and the patch is capable of monitoring the detected heartbeat and emitting the heartbeat signal independent of any external device.

2. The stand-alone continuous acoustic heart monitor patch of claim 1 wherein the heartbeat signal comprises a light source to emit light in response to the detected heartbeat.

3. The stand-alone continuous acoustic heart monitor patch of claim 2 wherein the light emitted in response to the detected heartbeat comprises a variable light intensity proportional to a strength of the detected heartbeat, and wherein the light emitted in response to the detected heartbeat further comprises an emergency light activated when the processor detects the absence of a heartbeat.

4. The stand-alone continuous acoustic heart monitor patch of claim 3 wherein the heartbeat signal further comprises a speaker to emit sound in response to the detected heartbeat.

5. The stand-alone continuous acoustic heart monitor patch of claim 4 wherein the sound emitted in response to the detected heartbeat comprises a variable sound intensity proportional to the strength of the detected heartbeat, and wherein the sound emitted in response to the detected heartbeat further comprises an emergency sound activated when the processor detects the absence of a heartbeat.

6. The stand-alone continuous acoustic heart monitor patch of claim 3 wherein the heartbeat signal further comprises a vibrator to emit a vibration in response to the detected heartbeat.

7. The stand-alone continuous acoustic heart monitor patch of claim 6 wherein the vibration emitted in response to the detected heartbeat comprises a variable vibration intensity proportional to the strength of the detected heartbeat, and wherein the vibration emitted in response to the absence of a heartbeat is an emergency vibration activated when the processor detects the absence of a heartbeat.

8. The stand-alone continuous acoustic heart monitor patch of claim 2 further comprising a switch to activate the circuitry from an inactive state.

9. The stand-alone continuous acoustic heart monitor patch of claim 8 wherein the switch is activated when the peel-away sheet is removed from the lower adhesive surface.

10. The stand-alone continuous acoustic heart monitor patch of claim 1 wherein the circuitry is incorporated onto a printed circuit board and wherein the base and the printed circuit board are flexible.

11. The stand-alone continuous acoustic heart monitor patch of claim 1 wherein the processor is further configured to monitor breathing by the patient or an absence of breathing from the sounds received by the microphone, and wherein the processor causes a breathing signal to be emitted indicative of the detected breathing.

12. The stand-alone continuous acoustic heart monitor patch of claim 11 wherein the processor causes an absence of breathing signal to be emitted indicative of the detected absence of breathing.

* * * * *